US006872856B2

(12) United States Patent
Blakemore et al.

(10) Patent No.: US 6,872,856 B2
(45) Date of Patent: Mar. 29, 2005

(54) CYCLIC KETONES, THEIR PREPARATION AND THEIR USE IN THE SYNTHESIS OF AMINO ACIDS

(75) Inventors: David Clive Blakemore, Kent (GB); Justin Stephen Bryans, Kent (GB)

(73) Assignee: Warner-Lambert Company, Morris Plains, NJ (US)

( * ) Notice: Subject to any disclaimer, the term of this patent is extended or adjusted under 35 U.S.C. 154(b) by 0 days.

(21) Appl. No.: 10/312,065

(22) PCT Filed: Jun. 28, 2001

(86) PCT No.: PCT/GB01/02900

§ 371 (c)(1),
(2), (4) Date: Feb. 5, 2003

(87) PCT Pub. No.: WO02/00584

PCT Pub. Date: Jan. 3, 2002

(65) Prior Publication Data

US 2003/0187296 A1 Oct. 2, 2003

(30) Foreign Application Priority Data

Jun. 28, 2000 (GB) ............................................. 0015771

(51) Int. Cl.⁷ ............................................... C07C 45/00
(52) U.S. Cl. ........................ 568/343; 568/356; 568/360
(58) Field of Search ................................ 568/343, 356, 568/360; 562/405, 404, 442

(56) References Cited

U.S. PATENT DOCUMENTS 5,254,708 A * 10/1993 Sato et al. ................... 556/436
5,434,238 A    7/1995 White et al. .................... 546/11

FOREIGN PATENT DOCUMENTS

WO           9921824      5/1999

OTHER PUBLICATIONS

Koelsch et al. Cis and Trans Forms of dl–3,4–Diethylpiperidine. Journal of the American Chemical Society (1944), 66, p 1881–1883.*
PCT International Search Report, PCT/GB01/02900.
Mase et al., "Diastereomer Differentiating Radical β–Addition to 4– or 5–Methyl–2–[(2,4,6–triisopropylphenyl)–sulfinyl]–2–cyclopentenones", *J. Org. Chem.*, vol. 63, No. 12, 1998, pp. 3899–3904.
Swanson et al., "Regioselective and Diastereoselective Alkyl–Alkene and Alkene–Alkene Coupling Protected by Zirconocene and Hafnocene", *J. Org. Chem.*, vol. 54, No. 13, 1989, pp. 3521–3523.
Smith et al, "Cuprate Additions to 5–Methoxycyclopentenones: A Novel Stereoelectronic Effect", *J. Org. Chem.*, vol. 29, No. 4, 1988, pp. 439–442.
Kokke and Varkevisser, "Two Syntheses of Optically Pure (1R,2R)–1,2–Dimethylcyclopentane", *J. Org. Chem.*, vol. 39, No. 11, 1974, pp. 1535–1539.

Battersby et al., "Ipecacuanha Alkaloids. Part VIII. Chemical Correlation of the Indole and Ipecacuanha Alkaloids", *J. Chem. Soc.*, No. 19, 1968, pp. 2467–2471.
Harre et al., "4–Oxo–2–cyclopentenyl Acetate—A Synthetic Intermediate", *Agnew. Chem. Int. Ed. Engl.*, No. 21, 1982, pp. 480–492.
Noyori, "Asymmetric Synthesis Via Axially Dissymmetric Molecules, a Binaphthol–Modified Complex Aluminum Hydride Reagent Possessing Extremely High Ability of Chiral Recognition", *Pure and Appl. Chem.*, vol. 53, 1981, pp. 2315–2322.
Johnson and Bis, "Enzymatic Asymmetrization of meso–2–Cycloalken–1,4–diols and Their Diacetates in Organic and Aqueous Media", *Tetrahedron Letters*, vol. 33, No. 48, 1992, pp. 7287–7290.
Kitamura et al., "Kinetic Resolution of 4–Hydroxy–2–cyclopentenone by Rhodium–Catalyzed Asymmetric Isomerization", *Tetrahedron Letters*, vol. 28, No. 40, 1987, pp. 4719–4720.
Watson et al., "Development of the Carbocyclic Nucleoside MDL 201449A: A Tumor Necrosis Factor–α Inhibitor", *Organic Process Research & Development*, vol. 2, 1998, pp. 357–365.
Khanapure et al., "An Efficient Synthesis of 4(S)–Hydroxycyclopent–2–enone", *J. Org. Chem.*, vol. 60, No. 23, 1995, pp. 7548–7551.
Ghorpade et al., "Enzymatic kinetic resolution studies of racemic 4–hydroxycyclopent–2–en–1–one using Lipozyme 1M®", *Tet rahedron: Asymmetry*, vol. 10, 1999, pp. 4115–4122.
Noyori et al., "Rational Designing of Efficient Chiral Reducing Agents. Highly Enantioselective Reduction of Aromatic Ketones by Binaphthol–Modified Lithium Aluminum Hydride Reagents", *J. Am. Chem. Soc.*, vol. 106, No. 22, 1984, pp. 6709–6716.
Noyori et al., "Synthetic Applications of the Enantioselective Reduction by Binaphthol–Modified Lithium Aluminum Hydride Reagents", *J. Am. Chem. Soc.*, vol. 106, No. 22, 1984, pp. 6717–6725.
Suzuki et al., "A Facile Synthesis of (–)–Prostaglandin E via a Three–Component Coupling Process", *Tetrahedron Letters*, vol. 23, No. 39, 1982, pp. 4057–4060.
Wu et al., "Highly Diastereoselective, Enantioselective Cyclization of Symmetrical 3,4–Disubstituted 4–Pentenal Using Chiral Rhodium(I)–complex", *Tetrahedron Letters*, vol. 34, No. 37, 1993, pp. 5927–5930.

* cited by examiner

*Primary Examiner*—Samuel Barts
*Assistant Examiner*—Sikarl A. Witherspoon
(74) *Attorney, Agent, or Firm*—Mehdi Ganjeizadeh

(57) ABSTRACT

A method is provided for making an enantiomerically pure compound of the formula: in which R and R' represent C1?C10 alkyl, C2?C10 alkenyl or C3?C10 cycloalkyl and the wedges signify (S)- or (R)-stereochemistry, the substituents in compound (II) being trans. Conjugate addition is carried out between an organometallic nucleophile that provides a group R as defined above and (R)-4-acetoxycyclopent-2-en-1-one, (S)-4-acetoxycyclopent-2-en-1-one or a similar compound in which acetoxy is replaced by another leaving group to give, e.g. in the case of the acetoxy compound, a trans 3,4-disubstituted addition product of formula III or IV; The acetyl group is eliminated from the addition product to give an (R)- or (S)-4-alkyl or 4-alkenyl cyclopent-2-en-1-one the compound of formula is then to be hydrogenated to give a cyclopentanone of formula (I) or conjugate addition of a second organometallic nucleophile that provides a group R' as defined above to the compound of the above formula may be carried out to give a trans 3,4-disubstituted addition product of formula (II). One of the above compounds may be converted e.g. via an intermediate (XV)–(XVIII) (in which the substituents R and R' and the wedges have the meanings indicated above) to a gabapentin analogue of one of the formulae shown below: in which the substituents R and R' and the wedges also have the meanings indicated above.

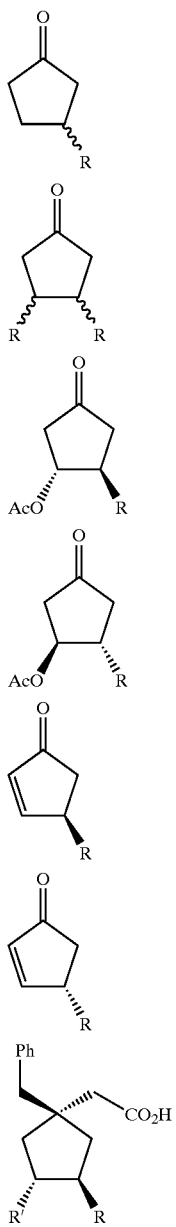
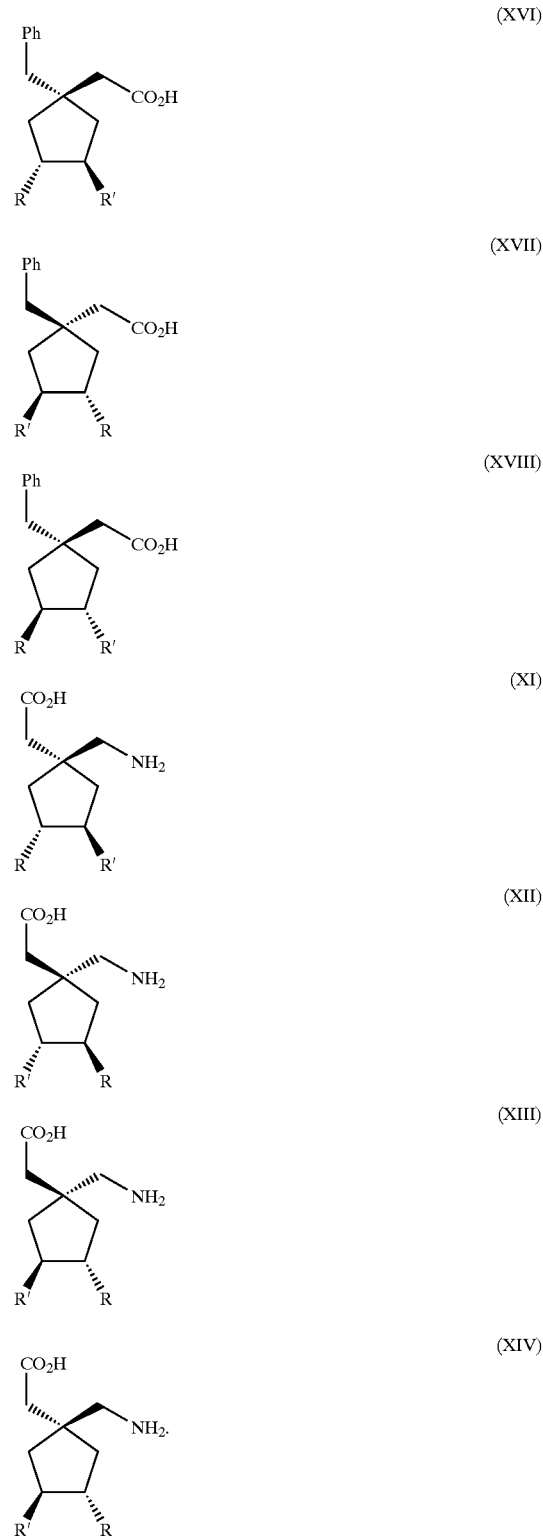

19 Claims, No Drawings

CYCLIC KETONES, THEIR PREPARATION AND THEIR USE IN THE SYNTHESIS OF AMINO ACIDS

FIELD OF THE INVENTION

The present invention relates to methods for the synthesis of alkyl- and alkenyl- and cycloalkyl-substituted cyclopentanones that are useful inter alia as intermediates for the synthesis of analogues of gabapentin (Neurontin®). It also relates to methods for the synthesis of gabapentin analogues using these intermediates, and also to certain novel intermediates per se.

BACKGROUND TO THE INVENTION

Gabapentin (Neurontin®) is an anti-convulsant agent that is useful in the treatment of epilepsy and that has recently been shown to be a potential treatment for neurogenic pain. It is 1-(aminomethyl)-cyclohexaneacetic acid of structural formula:

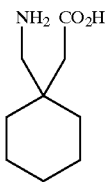

Gabapentin is one of a series of compounds of formula

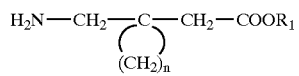

in which $R_1$ is hydrogen or a lower alkyl radical and n is 4, 5, or 6. These compounds are described U.S. Pat. No. 4,024,175 and its divisional U.S. Pat. No. 4,087,544. Their disclosed uses are: protective effect against cramp induced by thiosemicarbazide; protective action against cardiazole cramp; the cerebral diseases, epilepsy, faintness attacks, hypokinesia, and cranial traumas; and improvement in cerebral functions. The compounds are useful in geriatric patients. The disclosures of the above two patents are hereby incorporated by reference.

WO 99/21824, whose disclosure is also incorporated by reference, discloses further cyclic amino acids that are useful in the treatment of epilepsy, faintness attacks, neurodegenerative disorders, depression, anxiety, panic, pain, neuropathological disorders, gastrointestinal disorders such as irritable bowel syndrome (IBS) and inflammation, especially arthritis. The compounds disclosed include those of the formula:

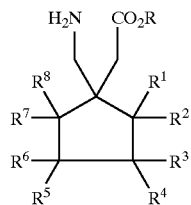

and salts thereof, in which:

R is hydrogen or a lower alkyl;

$R^1$ to $R^8$ are each independently selected from hydrogen, straight or branched alkyl of from 1 to 6 carbons, phenyl, benzyl, fluorine, chlorine, bromine, hydroxy, hydroxymethyl, amino, aminomethyl, trifluoromethyl, $—CO_2H$, $—CO_2R^{15}$, $—CH_2CO_2H$, $—CH_2CO_2R^{15}$, $—OR^{15}$ wherein $R^{15}$ is a straight or branched alkyl of from 1 to 6 carbons, phenyl, or benzyl, and $R^1$ to $R^8$ are not simultaneously hydrogen.

The compounds of WO 99/21824 may be synthesized:

using a general strategy (General Scheme 1) outlined by G. Griffiths et al., *Helv. Chim. Acta*, 1991; 74:309;

analogously to the published procedure for the synthesis of 3-oxo-2,8-diazaspiro[4,5]decane-8-carboxylic acid tert-butyl ester, see P. W. Smith et al., *J. Med. Chem.*, 1995; 38:3772 (General Scheme 2);

by the methods outlined by G. Satzinger et al., (Ger Offen 2,460,891; U.S. Pat. No. 4,024,175, and Ger Offen 2,611,690; U.S. Pat. No. 4,152,326) (General Schemes 3 and 4);

by a route outlined by G. Griffiths et al., *Helv. Chim. Acta*, 1991; 74:309 (General Scheme 5).

General Scheme 1

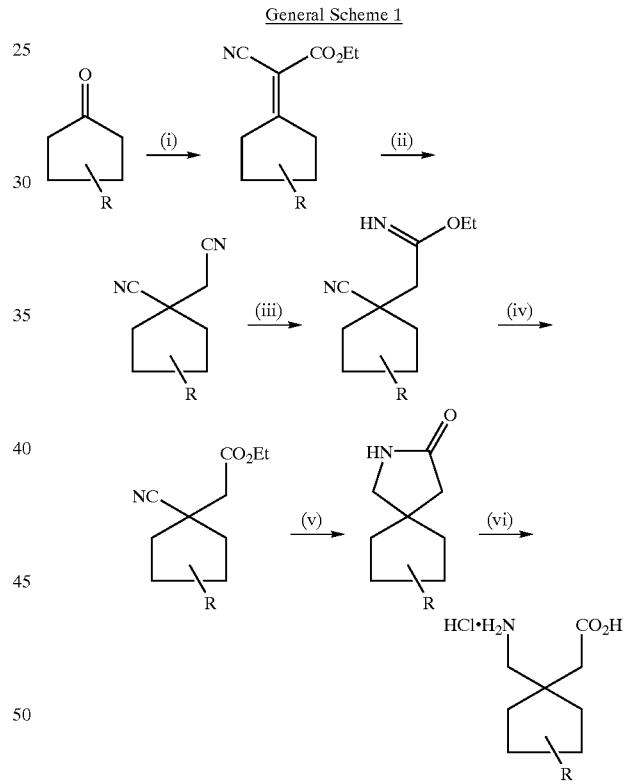

(i) Ethyl cyanoacetate, piperidine (Cope et al., *J. Am. Chem. Soc.*, 1941; 63:3452); (ii) NaCN, EtOH/$H_2O$; (iii) EtOH, HCl; (iv) $H_2O$/$H^+$; (v) $H_2$, Rh/C, MeOH; (vi) HCl.

General Scheme 2

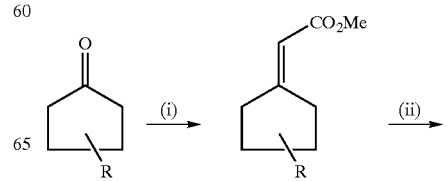

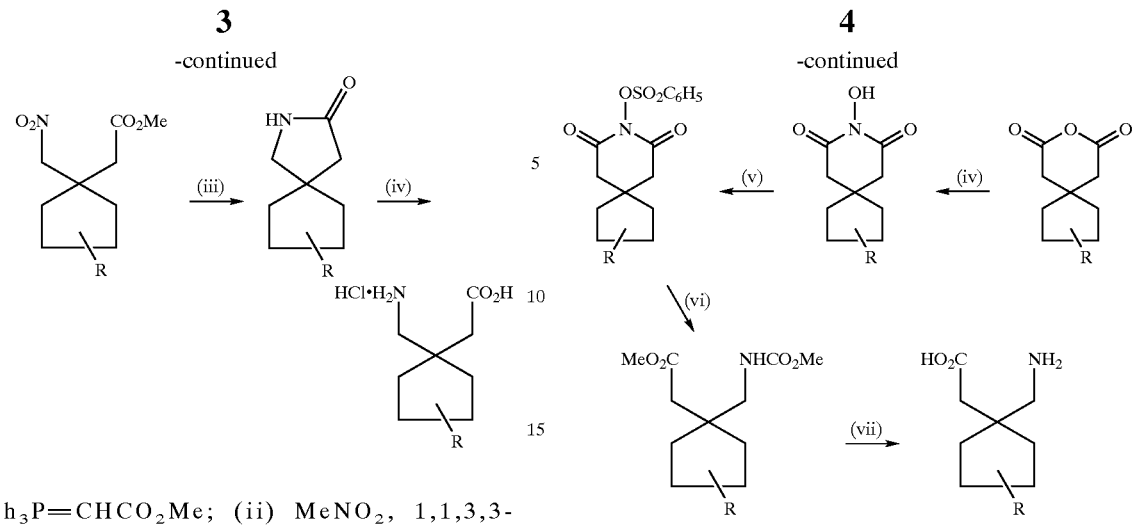

(i) $Ph_3P=CHCO_2Me$; (ii) $MeNO_2$, 1,1,3,3-tetramethylguanidine; (iii) Raney nickel, $EtOH/H_2O$; (iv) HCl.

(i) Ethylcyanoacetate, ammonia then $H_3O^+$; (ii) $H_2SO_4$; (iii) $Ac_2O$; (iv) $H_2NOH$; (v) $PhSO_2Cl$; (vi) $Et_3N$, MeOH; (vii) HCl, $H_2O$ then anion exchange.

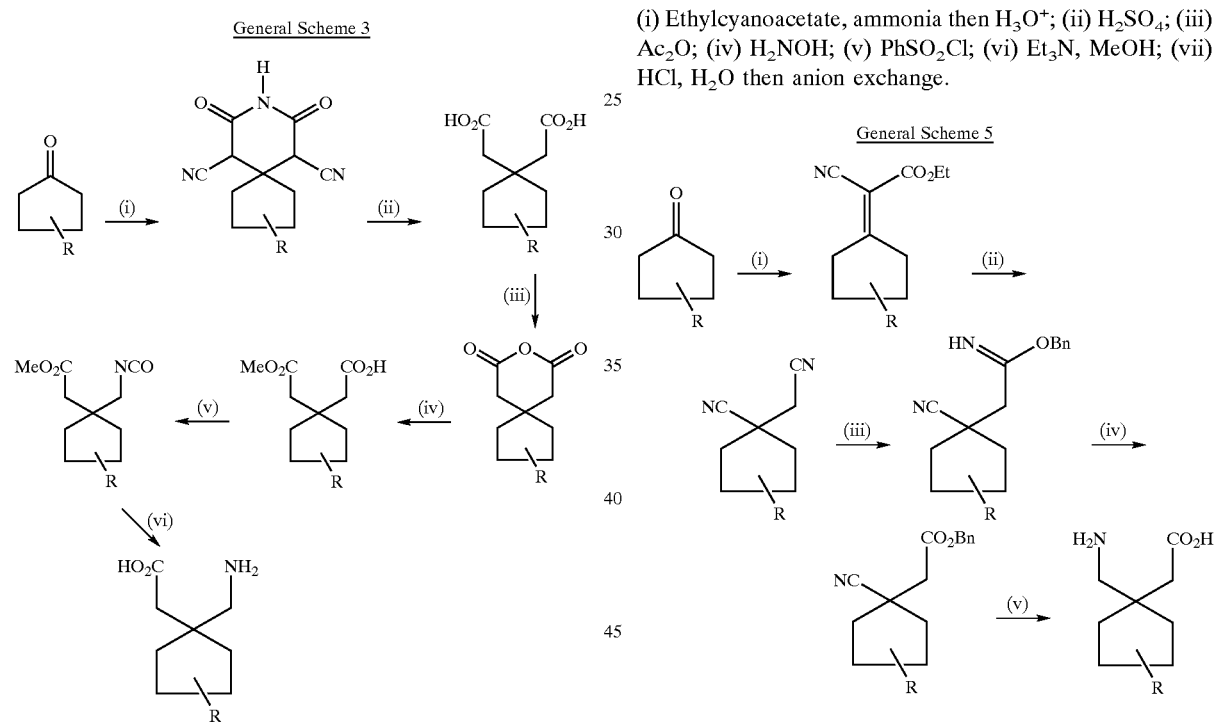

(i) Ethylcyanoacetate, ammonia then $H_3O^+$; (ii) $H_2SO_4$; (iii) $Ac_2O$; (iv) MeOH; (v) Curtius Reaction; (vi) HCl, $H_2O$ then anion exchange.

(i) Ethyl cyanoacetate, piperidine (Cope et al., *J. Am. Chem. Soc.*, 1941; 63:3452); (ii) NaCN, $EtOH/H_2O$; (iii) BnOH, HCl; (iv) $H_2O/H^+$; (v) $H_2$, Rh/C, MeOH.

Intermediates disclosed in WO 99/21824 include the following:

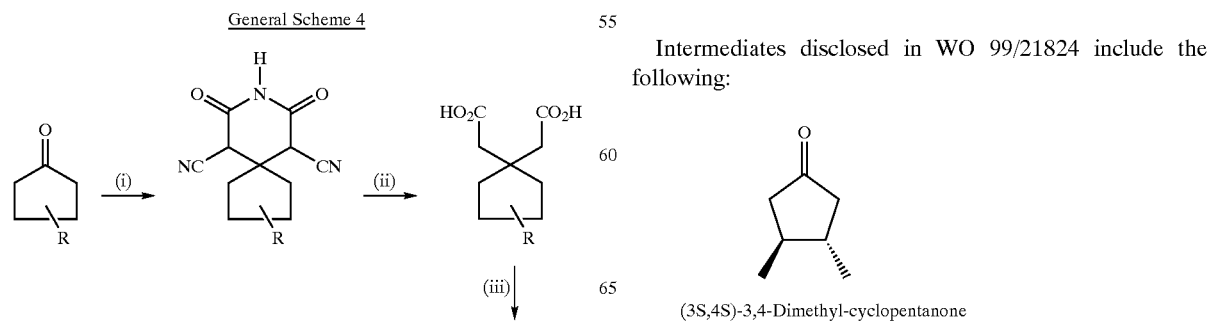

(3S,4S)-3,4-Dimethyl-cyclopentanone

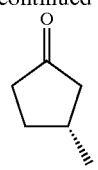

(R)-3-Methyl-cyclopentanone
and

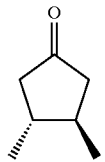

(3R,4R)-3,4-Dimethyl-cyclopentanone

Our U.S. patent application Ser. No. 60/169602, the disclosure of which is also incorporated herein by reference, describes and claims methods for the stereocontrolled synthesis of five-member ring Gabapentin analogues that are pure stereoisomers of compounds of formulae shown below and to salts thereof.

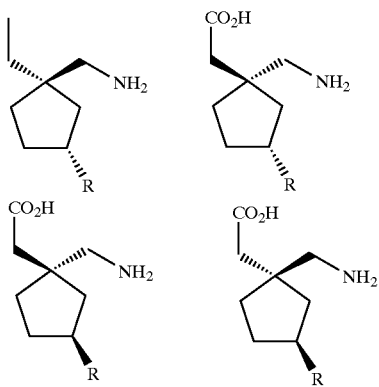

wherein R represents $C_1$–$C_{10}$ alkyl and $C_3$-$C_{10}$ cycloalkyl. The synthesis starts with the Knoevenagel condensation of a 3-substituted cyclopentanone of the kind described above with ethyl cyanoacetate and proceeds via the key intermediates

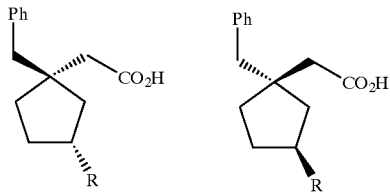

A method for preparing a compound of formula (7) in the following reaction scheme and pharmaceutically acceptable salts thereof comprises:

a) adding ethyl cyanoacetate to a mixture of a chiral cyclopentanone of formula (1) in a solvent to which a $C_1$–$C_6$ carboxylic acid and an amphoteric catalyst were added, and stirring the mixture to produce the alkene of formula (2);

b) adding the product of Step a) above to a mixture of benzylmagnesium chloride in a dry solvent to produce the addition product of formula (3);

c) adding the product of Step b) above to a mixture of a base in a solvent and stirring the mixture to produce the carboxylic acid of formula (4);

d) contacting the product of Step c) above with (S)-α-methyl-benzylamine in a solvent, and recrystallizing the salt so formed to produce the enriched diastereomer of formula (5) as the (S)-α-methyl-benzylamine salt;

e) adding the product of Step d) to an inorganic acid dissolved in a solvent and stirring to produce the carboxylic acid of formula (6);

f) adding the product of Step e) to a mixture of iodomethane in a solvent to which 1,8-diazabicyclo[5.4.0]undec-7-ene (DBU) was added, and stirring to produce the ester of formula (7);

g) adding the product of Step f) to a mixture of carbon tetrachloride and acetonitrile to which water, sodium periodate, and ruthenium(II) chloride were added, and stirring to produce the carboxylic acid of formula (8);

h) adding the product of Step g) to a mixture of an amine base and a solvent to which diphenylphosphoryl azide (DPPA) was added, and stirring to produce the isocyanate of formula (9);

i) adding the product of Step h) to a solvent to which methanol was added, and stirring to produce the carbamate of formula (10);

j) adding the product of Step i) to a solvent to which aqueous hydrochloric acid was added, and stirring to produce a compound of Formula Ia;

k) converting the product of Step j) to a compound of Formula I, and further converting, if desired, to a pharmaceutically acceptable salt by known means:

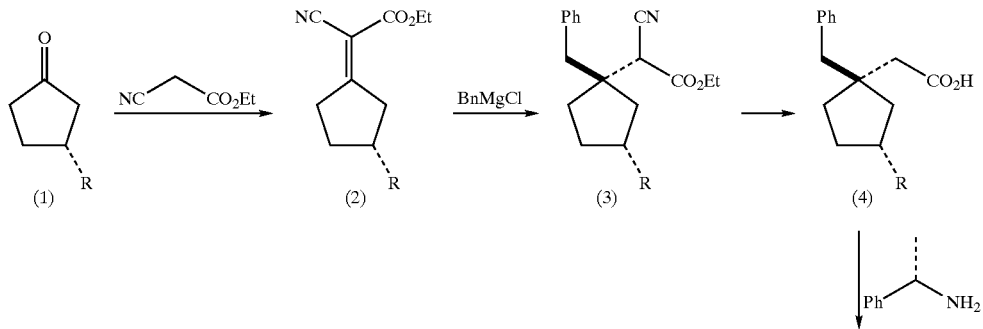

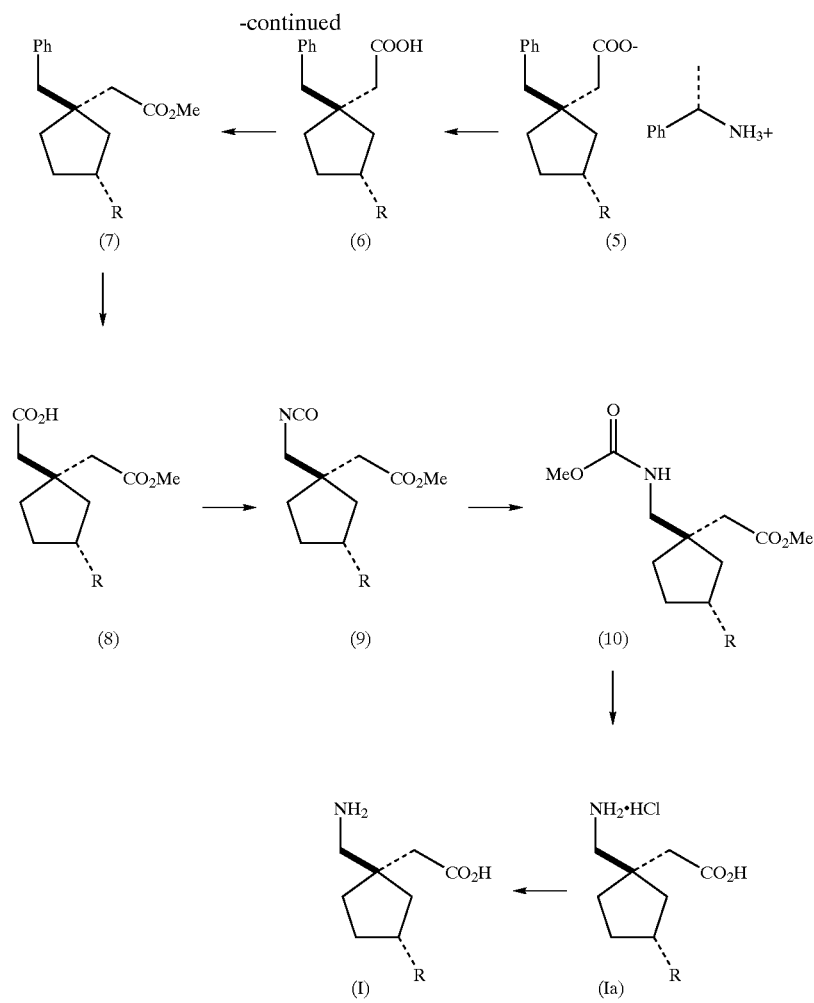

Preparation of a compound of formula II can proceed by a method which involves following the above-described sequence of steps (a) to (e) to produce the intermediate of step (6), and thereafter following the further steps indicated below:

f) adding the product of Step e) to a mixture of an amine base and a solvent to which diphenylphosphoryl azide (DPPA) was added, and stirring to produce the isocyanate of formula (11);

g) adding the product of Step f) to a solvent to which methanol was added and stirring to produce the carbamate of formula (12);

h) adding the product of Step g) to a mixture of carbon tetrachloride and acetonitrile to which water, sodium periodate, and ruthenium(III) chloride were added, and stirring to produce the carboxylic acid of formula (13);

i) adding the product of Step h) to a solvent to which aqueous hydrochloric acid was added, and stirring to produce a compound of Formula IIa;

k) converting the product of Step i) to a compound of Formula II, and further converting, if desired, to a pharmaceutically acceptable salt by known means:

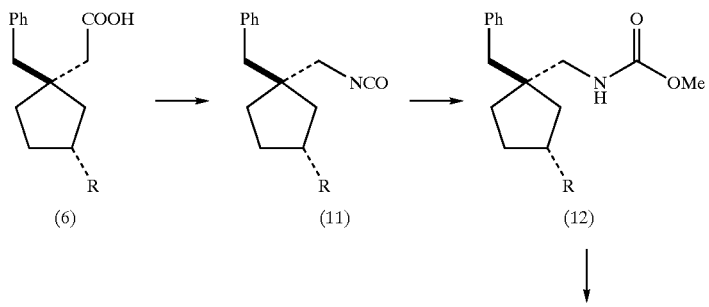

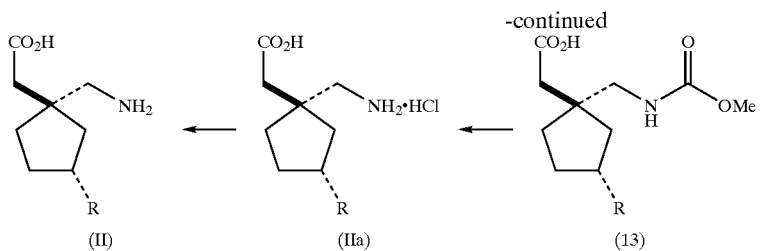

An alternative route to the compounds of formula (II), also proceeding from compound (6) above involves the further steps of:

f) adding oxalyl chloride to a mixture of the product of Step e) and a solvent to which N,N-dimethylformamide (DMF) was added, and stirring to produce the acid chloride of formula (14);

g) adding the product of Step f) to a mixture of tert-butyl alcohol in a solvent to which an amine base was added, and stirring to produce the ester of formula (15);

h) adding the product of Step g) to a mixture of carbon tetrachloride and acetonitrile to which water, sodium periodate, and ruthenium(III) chloride were added, and stirring to produce the carboxylic acid of formula (16);

i) adding the product of Step h) to a solvent to which methanol and (trimethylsilyl)diazomethane were added, and stirring to produce the bis ester of formula (17);

j) adding an acid to a mixture of the product from Step i) and a solvent and stirring to produce the carboxylic acid of formula (18);

k) adding the product of Step j) to a mixture of an amine base and a solvent to which diphenylphosphoryl azide (DPPA) was added, and stirring to produce the isocyanate of formula (19);

l) adding the product of Step k) to a solvent to which methanol was added and stirring to produce the carbamate of formula (20);

m) adding the product of Step l) to a solvent to which aqueous hydrochloric acid was added, and stirring to produce a compound of Formula IIa;

n) converting the product of Step m) to a compound of Formula II, and further converting, if desired, to a pharmaceutically acceptable salt by known means:

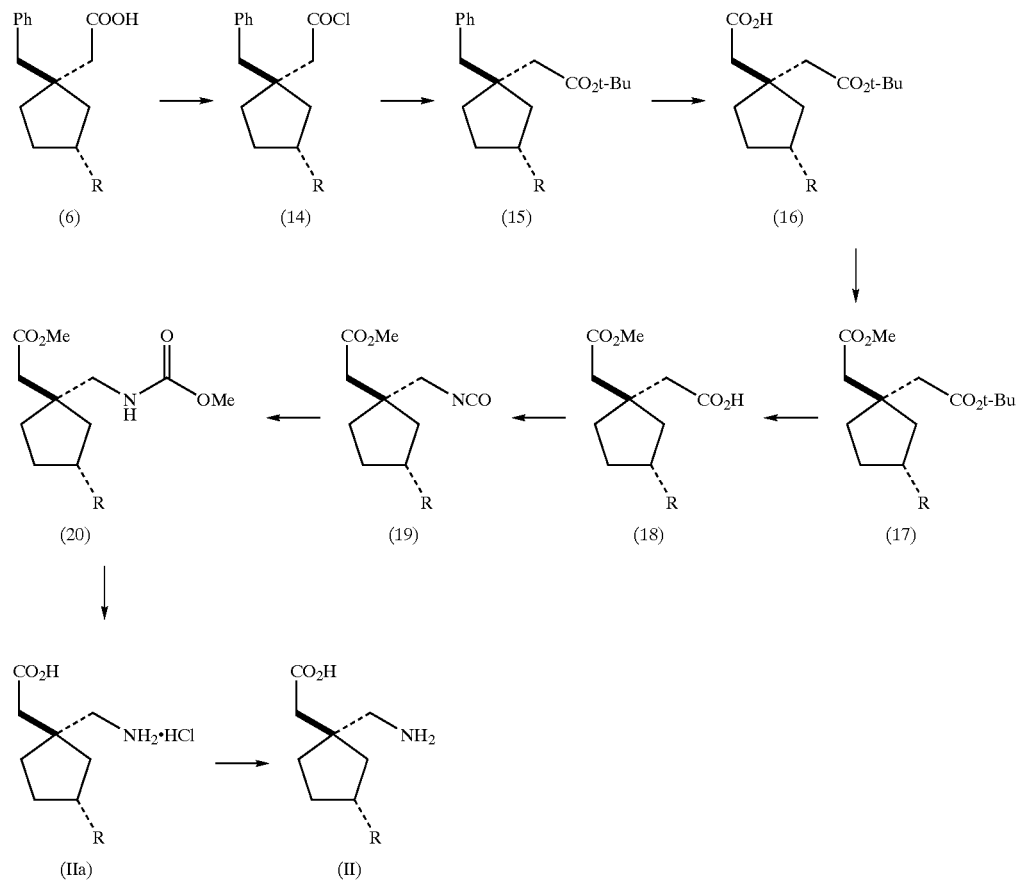

Compounds of formula (III) can be prepared by processes that involve the same steps as those for the compounds of formula (I), for example by following the sequence of reactions set out below:
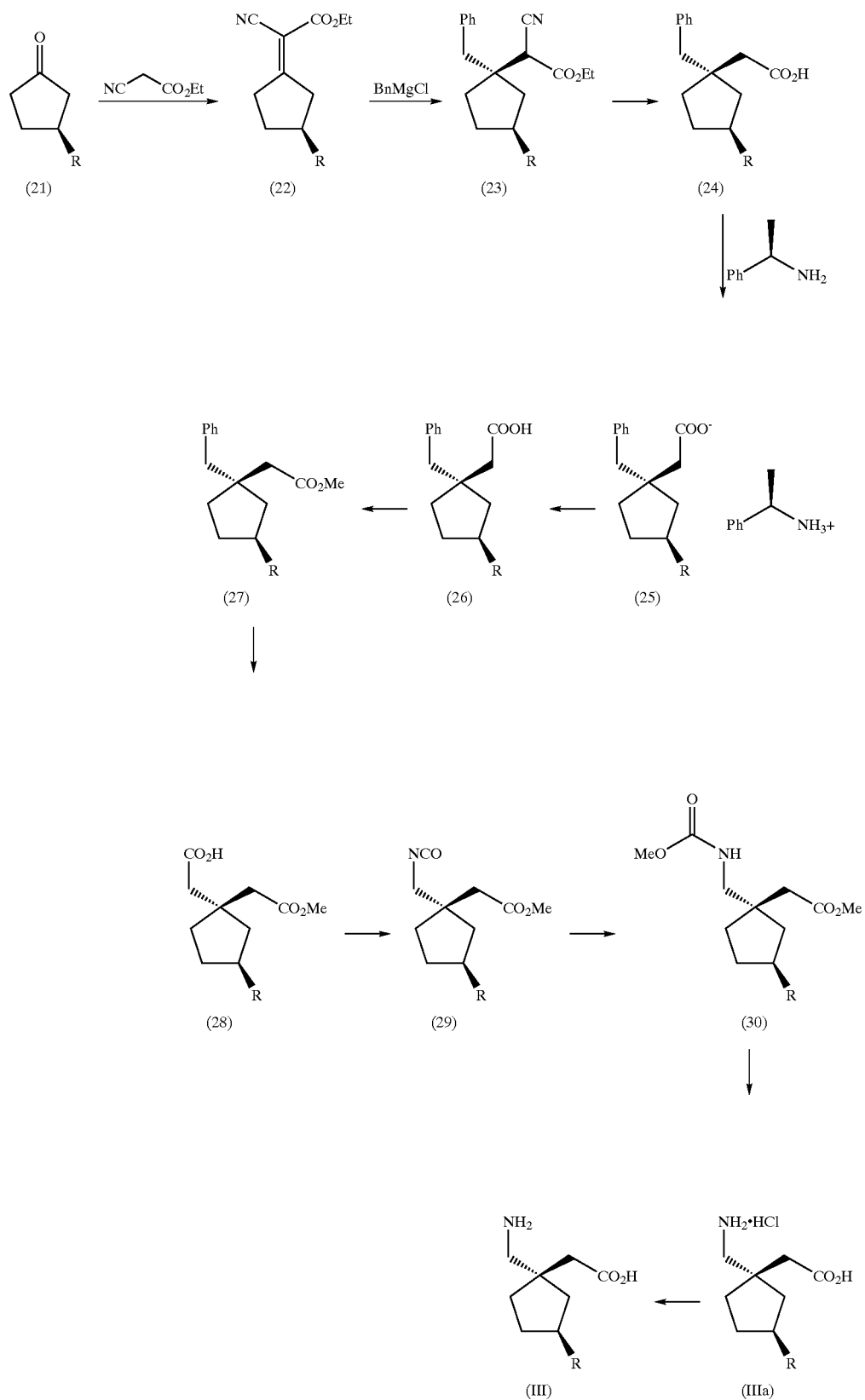

Similarly, compounds of formula (IV) may be made by a sequence of reactions analogous to those described above:
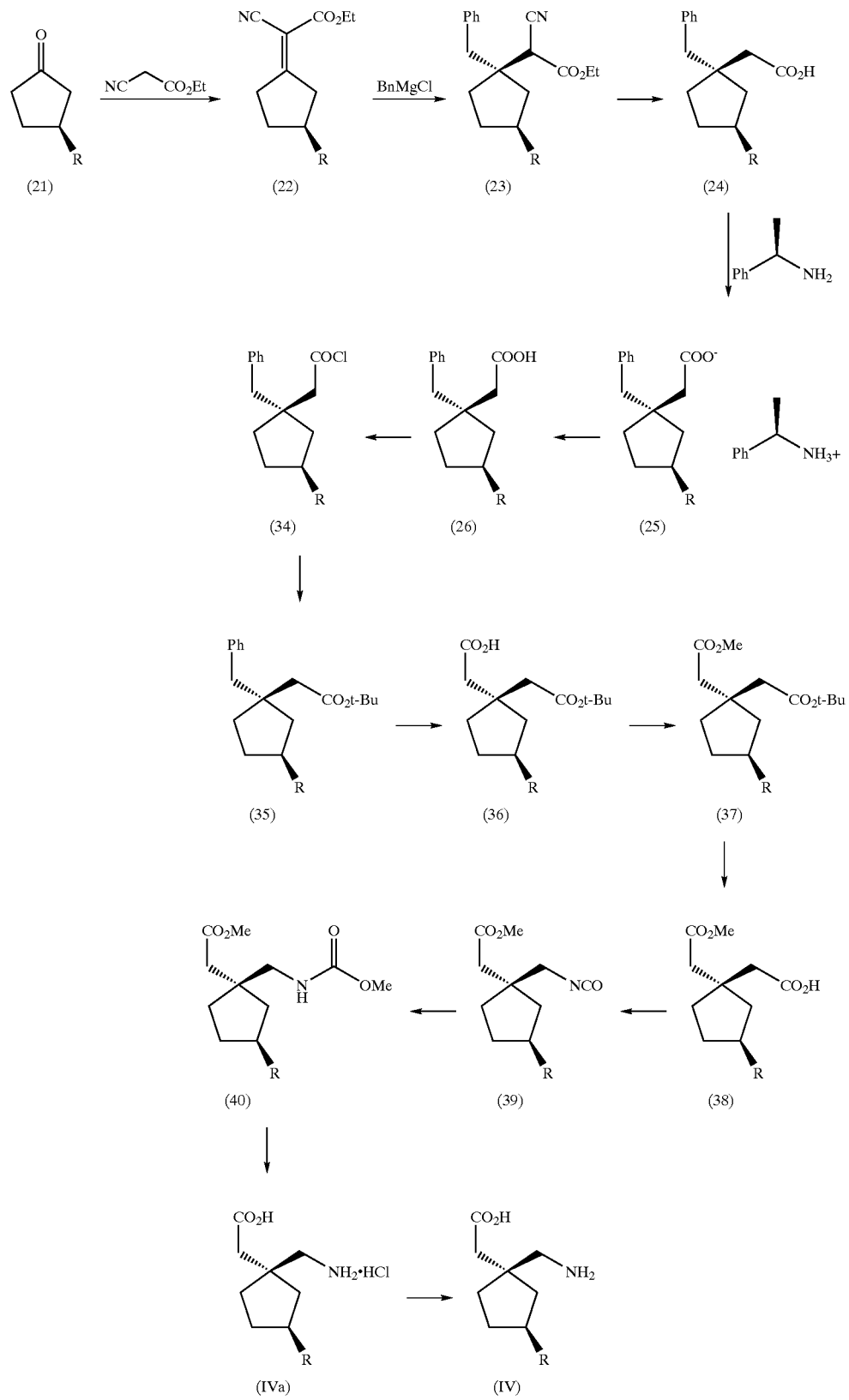

It will be noted that the synthetic methods disclosed in both WO 99/21824 and U.S. Ser. No. 60/169,602 rely on 3- or 3,4-substituted cyclopentanones.

SUMMARY OF THE INVENTION

This invention is concerned with the problem that the cyclopentanones available up to now have been limited in their range of stereoisomers and substituents because they have been derived from natural sources, or have been complex. For example, (R)-3-methyl-cyclopentanone is a compound that is readily available commercially from natural sources, whereas (S)-3-methyl-cyclopentanone is not. It is an object of the invention to provide a simple stereospecific synthetic route to 3-substituted or 3,4-disubstituted cyclopentanones that permits a range of desired substituents to be introduced and a range of desired stereoisomers to be made.

That problem is solved, according to the invention, by a process method of making an enantiomerically pure compound of the formula (I) or (II):

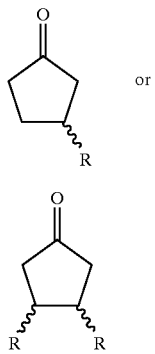

(I)

(II)

wherein R and R' represent $C_1$–$C_{10}$ alkyl, $C_2$–$C_{10}$ alkenyl or $C_3$–$C_{10}$ cycloalkyl and the wedges signify (S)- or (R)- stereochemistry, the substituents in compound (II) being trans, which method comprises:

conjugate addition of an organometallic nucleophile that provides a group R as defined above to a compound of the formula (III) or (IV):

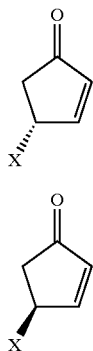

(III)

(IV)

wherein X represents a leaving group (e.g. an acetoxy group as in (R)-4-acetoxycyclopent-2-en-1-one or (S)-4-acetoxycyclopent-2-en-1-one) to give a trans 3,4-disubstituted addition product of formula (V) or (VI) in which R and X are as previously defined;

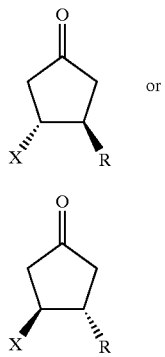

(V)

(VI)

eliminating the leaving-group from the addition product of formula (V) or (VI) to give an (R)- or (S)-4-alkyl or 4-alkenyl cyclopent-2-en-1-one of formula (VII) or (VIII)

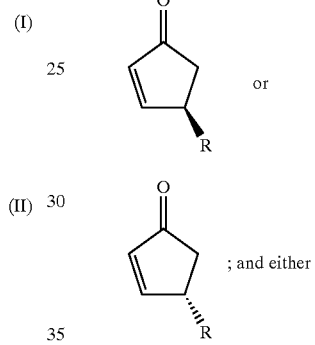

(VII)

(VIII)

; and either (i) hydrogenation of the compound of formula (VII) or (VIII) to give a cyclopentanone of formula (I) or (ii) conjugate addition of a second organometallic nucleophile that provides a group R' as defined above to the compound of formula (VII) or (VIII) to give a trans 3,4-disubstituted addition product of formula (II).

While conjugate addition to conjugated cyclopentenones is known for soft nucleophiles such as enolates, sulfides and bromides, such reactions have not been carried out with carbon-based nucleophiles with a view to producing chirally pure ketones. The group AcO— in the starting material brings about stereospecific addition of the group R during the first Michael addition, and where a second Michael addition is carried out, the group R that is already present in the compound of formula (VII) or (VIII) brings about stereospecific addition of the group R'. The enantiomeric purity of the resulting compounds of formula (I) and (II) can be tested by reacting them with an asymmetric diol such as (2R,3R)-2,3-butanediol to give an acetal having an additional asymmetric centre in the molecule, e.g

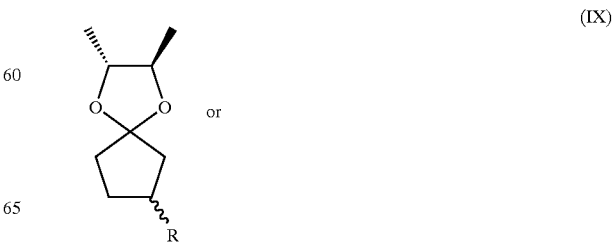

(IX)

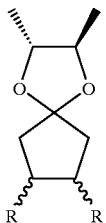

(X)

and obtaining the NMR spectrum of the resulting chiral acetal. If the starting material is an enantiomeric mixture, then the two resulting cyclic acetals will be diastereomeric and give distinguishable peaks in the NMR spectrum provided that the enantiomeric impurity is present in an amount of 2% or above. No such peaks have been observed in the materials that we have made, and we therefore believe that the method of the invention gives desired enantiomers with a purity of at least 98%.

According to a further aspect of the invention, a compound of formula (I) and (II) may be converted in manner known per se to a gabapentin analogue of one of the formulae shown below:

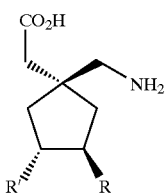

(XI)

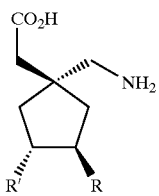

(XII)

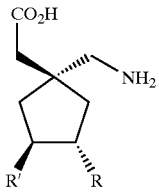

(XIII)

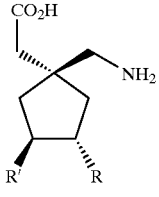

(XIV)

in which the substituents R and R' and the wedges have the meanings indicated above, and may be further converted into a pharmaceutically acceptable salt thereof.

Conversion to a compound of formula (XI)–(XIV) may, for example, follow one of the general schemes disclosed in WO 99/21824, or it may follow the Knoevenagel addition route disclosed in U.S. Ser. No. 60/169,602. In the latter case, there may be produced the key intermediates (XV)–(XVIII) shown below:

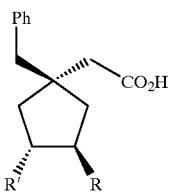

(XV)

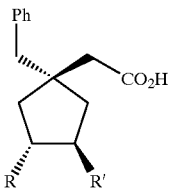

(XVI)

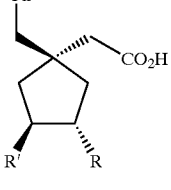

(XVII)

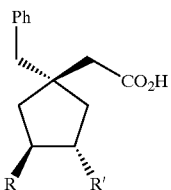

(XVIII)

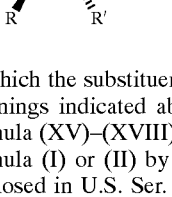

in which the substituents R and R' and the wedges have the meanings indicated above. Thereafter, the intermediate of formula (XV)–(XVIII) may be converted to a compound of formula (I) or (II) by one of the three principal strategies disclosed in U.S. Ser. No. 60/169,602, i.e. (i) transforming the phenyl ring to a carboxylic acid and then to an amine; (ii) transforming the carboxylic acid group into an amine and oxidizing the phenyl group to an acid, or (iii) protecting the carboxylic acid group, oxidizing the phenyl ring to a second carboxylic acid group, protecting the second carboxylic acid group, selectively de-protecting the first carboxylic acid group, transforming the first carboxylic acid group to an amine, and deprotecting the second carboxylic acid group.

Certain of the present intermediates are believed to be new. In a farther aspect, therefore, the invention provides enantiomerically pure compounds of the formula:

(II)

wherein R and R' represent $C_1$–$C_{10}$ alkyl, $C_2$–$C_{10}$ alkenyl or $C_3$–$C_{10}$ cycloalkyl and the wedges signify (S)- or (R)-stereochemnistry, the substituents being trans, and at least one of R and R' not being methyl.

DESCRIPTION OF PREFERRED FEATURES

As previously stated, the compounds of the invention can be prepared in chirally pure form from (R)-4- acetoxycyclopent-2-en-1-one (1) or (S)-4-acetoxycyclopent-2-en-1-one (2).

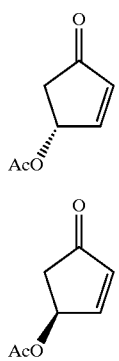

The reactions of 4-Oxo-2–Cyclopentenyl Acetate (4-Acetoxy-2–Cyclopenten-1-one) have been reviewed by M. Harre, P. Raddatz, R. Walenta and E. Winterfeldt, *Angew. Chem. Int. Ed. Engl.*, 1982, 21, 480. It has been synthesised in enantiomerically pure form using two main approaches:

Acetylation of chirally pure 4-hydroxy-2-cyclopenten-1-one, see K. Ogura, M. Yamashita and G. Tsuchihashi, *Tetrahedron Letters*, 1976, 759. For examples of approaches to chiral 4-hydroxy-2–Cyclopenten-1-one see the following and references therein: S. R. Ghorpade, K. B. Bastawade, D. V. Gokhale, P. D. Shinde, V. A. Mahajan, U. R. Kalkote and T. Ravindranathan, *Tetrahedron Asymmetry*, 1999, 10, 4115; S. P. Khanapure, N. Najafi, S. Manna, J-J. Yang and J. Rokach, *J. Org. Chem.*, 1995, 60, 7548; E. Mezzina, D. Savoia, E. Tagliavini, C. Trombini and A. Umani-Ronchi, *J. Chem. Soc. Perkin Trans.* 1, 1989, 845; M. Kitamura, K. Manabe and R. Noyori, *Tetrahedron Letters,* 1987, 28, 4719; R. Noyori, I. Tomino, M. Yamada and M. Nishizawa, *J. Am. Chem. Soc.*, 1984, 106, 6717; M. Suzuki, T. Kawagishi, T. Suzuki and R. Noyori, *Tetrahedron letters*, 1982, 23, 4057; R. Noyori, *Pure & Appl. Chem.*, 1981, 53, 2315; T. J. N. Watson, T. T. Curran, D. A. Hay, R. S. Shah, D. L. Wenstrup and M. E. Webster, *Organic Process Research & Development*, 1998, 2, 357; S. R. Ghorpade, K. B. Bastawade, D. V. Gokhale, P. D. Shinde, V. A. Mahajan, U. R. Kalkote and T. Ravindranathan, *Tetrahedron: Asymmetry*, 1999, 10, 4115–4122).

Oxidation of 3-acetoxy-5-hydroxycyclopent-1-enes, for example see: M. Korach, D. R. Nielsen and W. H. Rideout, *Org. Synth., Collect. Vol.* 5, 1973, 414; D. R. Deardoff and D. C. Myles, *Org. Synth.*, 1989, 67, 114; D. R. Deardorff, C. Q. Windham and C. L. Craney, *Org. Synth.*, 1995, 73, 25; C. R. Johnson and S. J. Bis, *Tetrahedron Letters*, 1992, 33, 7287.

The following reactions may be used to make compounds according to the invention:

A) Conjugate addition to a cyclopent-2-en-1-one (1) or (2) can be carried out using an organo-Grignard reagent in the presence of dimethylzinc giving a trans 3,4-disubstituted intermediate e.g. an addition product of formula (3) or (4). In particular, the chiral cyclopentenone of formula (1) or (2) may be added to the organo-Grignard reagent or to an organo-lithium reagent in the presence of a dialkylzinc or zinc chloride or a copper (I) salt or a trialkylaluminium in a solvent, for example, tetrahydrofuran, 1,4-dioxane, n-heptane, toluene, diethyl ether or tert-butyl methyl ether at a temperature from −100° C. to 0° C. to produce said addition product.

B) Adding the product of step A) above to a mixture of base, for example, 1,8-diazabicyclo[5.4.0]undec-7-ene (DBU), 1,5-diazabicyclo[4.3.0]non-5-ene (DBN), 1,1,3,3-tetramethyl guanidine (TMG), lithium hydride or sodium hydride in a solvent, for example, dichloromethane, diethyl ether, tetrahydrofuran, tert-butyl methyl ether or 1,4-dioxane to produce an elimination product of formula (5) or (6).

C) Adding the product of step B) above to a mixture of organo-Grignard reagent or organo-lithium reagent in the presence of a dialkylzinc or zinc chloride or a copper (I) salt or a trialkylaluminium salt in a solvent, for example, tetrahydrofuran, 1,4-dioxane, n-heptane, toluene, diethyl ether or tert-butyl methyl ether at a temperature from −100° C. to 0° C. can be used to produce an addition product of formula (7) or (8).

D) Adding the product of step B) above to a hydrogenation catalyst, for example, palladium on charcoal, platinum oxide, Raney nickel, Rhodium on alumina in a solvent, for example, ethyl acetate or methanol under a hydrogen atmosphere at 1 to 30 atmospheres pressure and at a temperature in the range 0–60° C., can be used to make a product of formula (9) or (10).

The above described reactions are illustrated in the following schemes:

Scheme 1

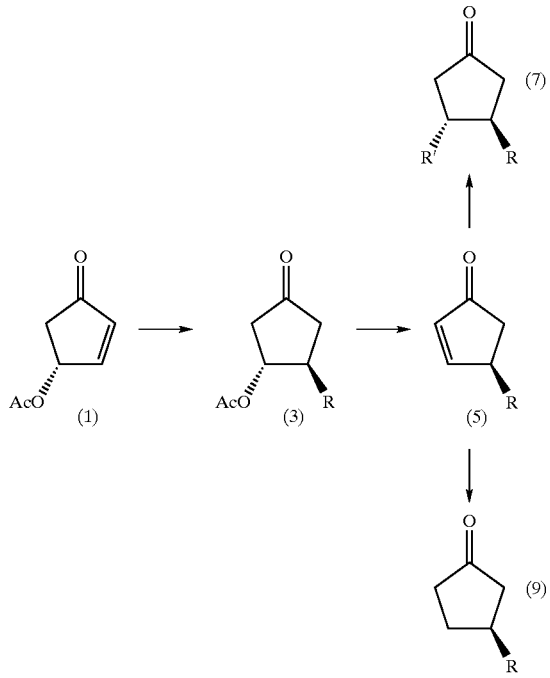

Scheme 2

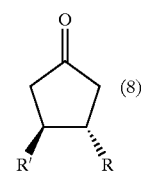

-continued

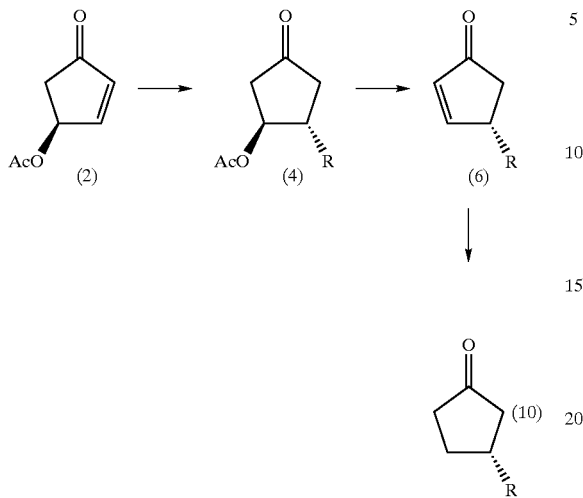

An example of the utility of the above reaction scheme is shown below:

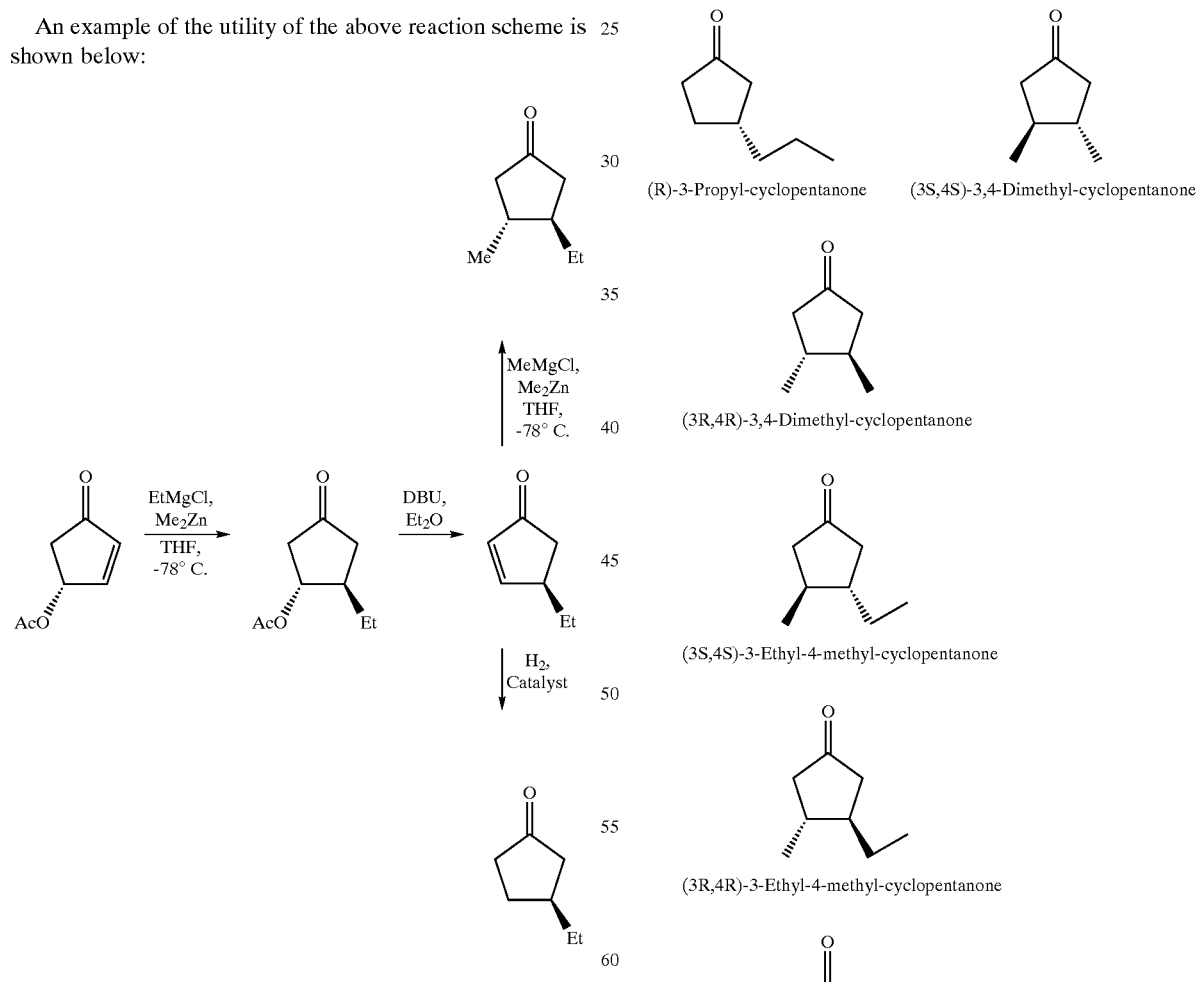

Compounds that can be made by the present process are shown below, and the following are believed to be new:
(3S,4S)-3,4-diethyl-cyclopentanone;
(3R,4R)-3,4-diethyl-cyclopentanone;
(3S,4S)-3-ethyl-4-methyl-cyclopentanone;
(3R,4R)-3-ethyl-4-methyl-cyclopentanone;
(3S,4S)-3-methyl-4-propyl-cyclopentanone;
(3R,4R)-3-methyl-4-propyl-cyclopentanone;
(3S,4S)-3-ethyl-4-propyl-cyclopentanone; and
(3R,4R)-3-ethyl-4-propyl-cyclopentanone.

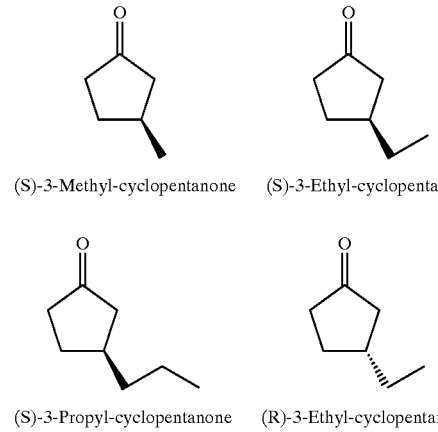

-continued

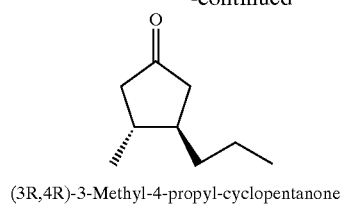

(3R,4R)-3-Methyl-4-propyl-cyclopentanone

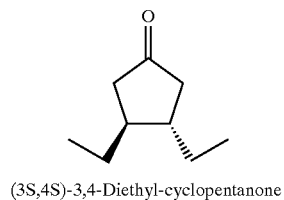

(3S,4S)-3,4-Diethyl-cyclopentanone

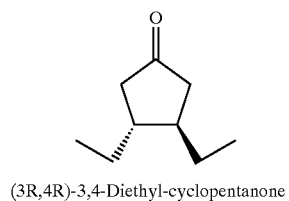

(3R,4R)-3,4-Diethyl-cyclopentanone

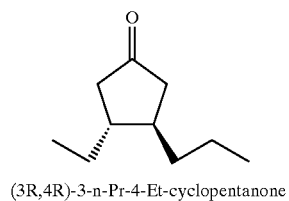

(3R,4R)-3-n-Pr-4-Et-cyclopentanone

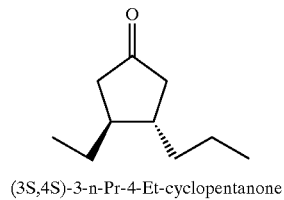

(3S,4S)-3-n-Pr-4-Et-cyclopentanone     (R)-3-Methyl-cyclopentanone

Other leaving groups may be present in the starting materials employed in the above process in place of the acetoxy compounds, and in general any compound that is available in optically pure form and that has a 4-substituent that permits stereospecific addition to the en-one conjugated system and can then undergo elimination can be used. Examples of such leaving groups are halides and sulfonic acid ester groups. Examples of alternative starting materials include:

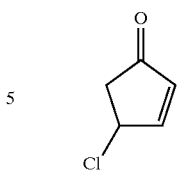

For preparation see T. Hirao, S. Mikami, M. Mori, Y. Ohshiro, *Tet. lett.*, 1991, 32(14), 1741–4. For stereospecific preparation of R and S enantiomers see R. Gerdil, H. Liu, G. Bernardinelli, *Helv. Chim. Acta.*, 1999, 82(3), 418–34.

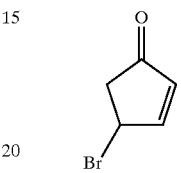

For preparation see: F. Gavina, A. Costero, A. Gonzalez, S. Luis, *J. Org. Chem.*, 1987, 52(14), 2997–9; C. H. DePuy, M. Isaks, K. L. Eilers, G. F. Morris, *J. Org. Chem.*, 1964, 29, 3503–10; J. A. Bloodworth, H. J. Eggelte, *J. Chem. Soc. Perkin Trans. I*, 1981, 12, 3272–8.

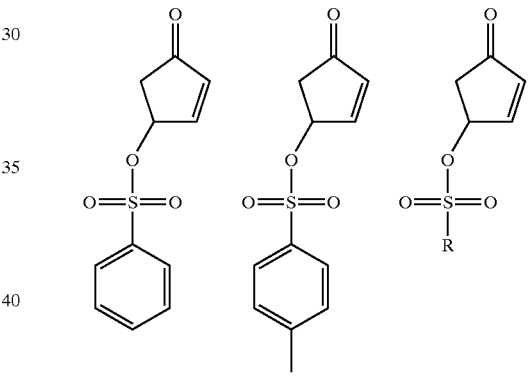

For preparation of the above two compounds or the class of compounds of the third formula, in which R=straight or branched alkyl of $C_1$–$C_6$, see M. Minamii, Y. Ueda, JP 62116537 (JP 85-262204), JP 85-167970 and M. Minamii, Y. Ueda, EP-A-0170506.

The invention will now be further described in the following Examples.

EXAMPLE 1

Enantiomerically pure (S)-3-n-propyl-cyclopentanone (3)

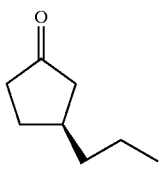

3

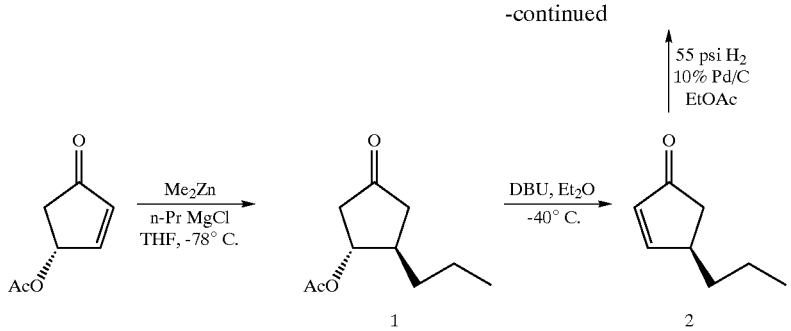

(3R,4R)-3-acetoxy-4-n-propyl-cyclopentanone (1)

n-Propylmagnesium chloride (15.7 ml of a 2M solution in ether, 31.4 mmol) was added slowly to a stirred solution of dimethylzinc (15.7 ml of a 2M solution in toluene, 31.4 mmol) in THF (80 ml) under argon at 0° C. After 30 minutes, the mixture was cooled to −78° C. and (R)-4-acetoxycyclopent-2-enone (4.0 g, 28.5 mmol) in THF (45 ml) was added dropwise over 1 hour. The reaction mixture was stirred for a further 20 minutes and then quenched by the addition of saturated ammonium chloride solution (20 ml). The reaction mixture was allowed to warm to room temperature, diluted with 1N hydrochloric acid (100 ml) and extracted with ether (3×200 ml). The organic layer was washed with brine (200 ml), dried (MgSO$_4$) and the solvent was removed under reduced pressure to yield the acetoxy cyclopentanone 1 as a solution in toluene which was used without further purification in the next step.

$v_{max}$(film)/cm$^{-1}$ 1740 (C=O).

$\delta_H$(400 MHz; CDCl$_3$) 5.08 (1H, m, CHOAc), 2.70 (1H, dd, J 19.2, 5.9), 2.59 (1H, dd, J 8.1, 1.2), 2.34 (1H, m), 2.23 (1H, dd, J 19.1, 4.6), 2.07 (3H, s, OCOMe), 1.98 (1H, dd, J 18.4, 6.4), 1.54 (1H, m), 1.46–1.21 (3H, m), 0.94 (3H, t, J 7.1, Me).

(R)-4-n-propyl-cyclopent-2-enone (2)

The acetoxy cyclopentanone 1 (approx. 28.5 mmol) in ether (40 ml) was added dropwise over 1 hr to a stirred solution of DBU (4.27 ml, 28.5 mmol) in ether (50 ml) at −40° C. under argon. The mixture was allowed to warm to −30° C. and stirred for 30 minutes before being quenched with dilute hydrochloric acid (20 ml). The reaction mixture was partitioned between ether (100 ml) and 1N HCl (150 ml). The organic layer was separated and the aqueous layer was further extracted with ether (2×100 ml). The combined ether layers were washed with brine, dried (MgSO$_4$) and the solvent was evaporated under reduced pressure. The residue was chromatographed (SiO$_2$, pentane-ether, 1:0 to 8:2) to give the propylcyclopentenone 2 (2.4 g, 68% from (R)-4-acetoxycyclopent-2-enone).

$v_{max}$(film)/cm$^{-1}$ 1708 (C=O).

$\delta_H$(400 MHz; CDCl$_3$) 7.64 (1H, dd, J 5.6, 2.4, CH=CHC=O), 6.14 (1H, dd, J 5.6, 2.0, CH=CHC=O), 2.75 (1H, m), 2.53 (1H, dd, J 18.8, 6.4, CH$_A$H$_B$C=O), 2.00 (1H, dd, J 18.8, 2.0, CH$_A$H$_B$C=O) 1.60–1.20 (4H, m), 0.96 (3H, t, J 6.8, Me).

(S)-3-n-propylcyclopentanone (3)

A mixture of 2 (1.2 g, 9.7 mmol) and 10% palladium on charcoal (catalytic quantity) in ethyl acetate (30 ml) was shaken in hydrogen at 55 psi and at 30° C. for 6 hours. The reaction mixture was filtered and the solvent was evaporated under reduced pressure. The residue was chromatographed (SiO$_2$, pentane-ether, 1:0 to 9:1) to give the 3-propylcyclopentanone 3 (1.07 g, 88%).

$v_{max}$(film)/cm$^{-1}$ 1744 (C=O).

$\delta_H$(400 MHz; CDCl$_3$) 2.29 (1H, dd, J 16.0, 8.4), 2.38 (1H, dd, J 18.8, 7.6), 2.21–2.09 (2H, m), 1.79 (1H, dd, J 18.0, 9.6), 1.56–1.34 (6H, m), 0.93 (3H, t, J 7.2, Me).

Enantiomeric Purity by Conversion to Acetal (7)

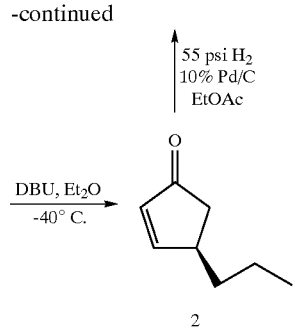

The ketone 3 (0.12 g, 0.95 mmol), (2R,3R)-(−)-2,3-butanediol (0.087 ml, 0.96 mmol) and p-toluenesulphonic acid (0.018 g, 0.095 mmol) were refluxed together in benzene (10 ml) for 3 hours using a Dean-Stark trap. The reaction mixture was allowed to cool, taken up in ethyl acetate (100 ml) and washed with saturated sodium bicarbonate solution, brine, dried (MgSO$_4$) and concentrated in vacuo to give a single diastereoisomeric acetal 7 (0.12 g, 65%).

$\delta_H$(400 MHz; CDCl$_3$) 3.61–3.57 (2H, m), 2.1–1.76 (5H, m), 1.47–1.40 (2H, m), 1.35–1.20 (10H, m), 0.88 (3H, t, J 6.8, Me); $\delta_C$(CDCl$_3$) 117.2, 78.3, 78.1, 44.6, 38.4, 37.6, 37.2, 30.1, 21.3, 17.2, 17.1, 14.2.

EXAMPLE 2

(3R,4R)-3-methyl-4-n-propyl-cyclopentanone (4)

Methylmagnesium chloride (7.1 ml of a 3M solution in ether, 21.3 mmol) was added slowly to a stirred solution of dimethylzinc (5.3 ml of a 2M solution in toluene, 10.6 mmol) in THF (80ml) under argon at 0° C. After 30 minutes the mixture was cooled to −78° C. and 2 (1.2 g, 9.7 mmol) in THF (45 ml) was added dropwise over 1 hour. The reaction mixture was stirred for 20 minutes and then quenched by the addition of saturated ammonium chloride solution (20 ml). The reaction mixture was allowed to warm to room temperature, diluted with 1N hydrochloric acid (100 ml) and extracted with ether (3×200 ml). The organic layer was washed with brine (200 ml), dried (MgSO$_4$) and the solvent was removed under reduced pressure to yield 4 as a solution in toluene which was purified by column chromatography (SiO$_2$, pentane-ether, 1:0 to 9:1 to give the cyclopentanone 4 (0.86 g, 63%).

$v_{max}$(CDCl$_3$)/cm$^{-1}$ 1733 (C=O).

$\delta_H$(400 MHz; CDCl$_3$) 2.49–2.42 (2H, m), 1.87–1.80 (3H, m), 1.79–1.61 (2H, m), 1.80–1.43 (3H, m), 1.12 (3H, d, J 6.1, Me), 0.93 (3H, t, J 7.3, Me); $\delta_C$(CDCl$_3$) 220.0, 48.1, 46.2, 45.5, 38.4, 37.0, 232.1, 19.6, 15.8.

Enantiomeric Purity by Conversion to Acetal 8

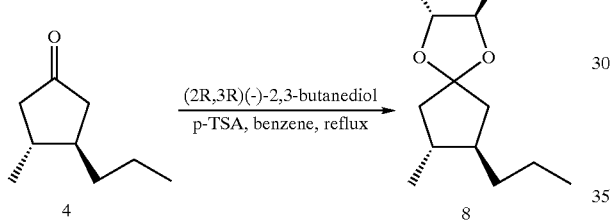

The ketone 4 (0.12 g, 0.86 mmol), (2R,3R)-(−)-2,3-butanediol (0.086 ml, 0.94 mmol) and p-toluenesulphonic acid (0.0163 g, 0.086 mmol) were refluxed together in benzene (10 ml) for 3 hours using a Dean-Stark trap. The reaction mixture was allowed to cool, taken up in ethyl acetate (100 ml), washed with saturated sodium bicarbonate solution, brine, dried (MgSO$_4$) and concentrated in vacuo to give 8 (0.08 g, 44%).

$\delta_H$(400 MHz; CDCl$_3$) 3.61–3.58 (2H, m), 2.51–2.39, 2.27, 2.19–2.06, 1.90–1.60 (6H, m), 1.60–1.04 (10H, m), 0.98 (3H, d, J 6.6, Me), 0.89 (3H, t, J 7.3, Me); $\delta_C$(400 MHz; CDCl$_3$) 115.8, 78.2, 78.1, 47.2, 45.1, 45.0, 38.4, 36.5, 21.4, 18.8, 17.3 (x2), 14.4.

EXAMPLES 3 & 4

(R)-3-n-propyl-cyclopentanone (5) and (3S,4S)-3-methyl-4-n-propyl-cyclopentanone (6)

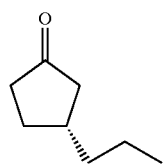

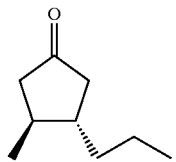

Ketones 5 and 6 were made using the same procedures as in the preceding examples, but starting from (S)-4-acetoxycyclopent-2-enone.

Enantiomeric Purity by Conversion to Chiral Acetals 9, 10

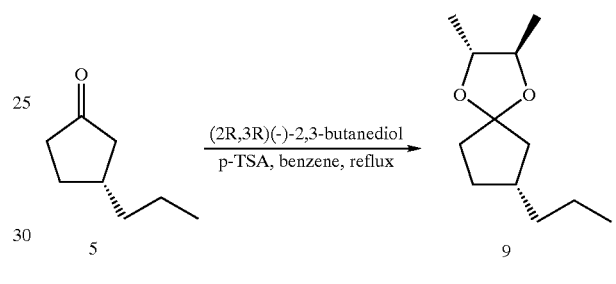

The enantiomeric purity of ketone 5 was confirmed by making acetal 9 using the procedure of the foregoing examples.

$\delta_H$(400 MHz; CDCl$_3$) 3.60–3.48 (2H, m), 2.45–1.76 (5H, m), 1.44–1.41 (2H, m), 1.38–1.14 (10H, m), 0.88 (3H, t, J 7.1, mE); $\delta_C$(CDCl$_3$) 117.2, 78.2, 78.1 44.9, 38.2, 38.0, 37.7, 30.5, 21.3, 17.0, 16.9, 14.2.

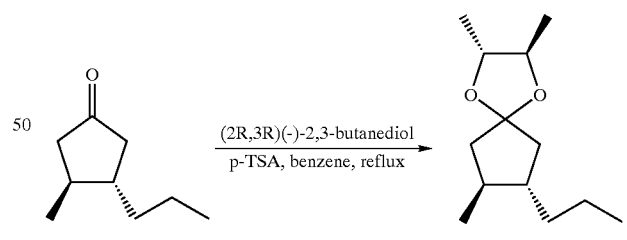

The enantiomeric purity of ketone 6 was confirmed by making acetal 10 using the procedure of the above examples.

$\delta_H$(400 MHz; CDCl$_3$) 3.56–3.49 (2H, m), 2.49–2.22, 2.13–2.04, 1.90–1.62 (6H, m), 1.60–1.02 (10H, m), 0.97 (3H, d, J 6.1, Me), 0.89 (3H, t, J 7.3, Me); $\delta_C$(CDCl$_3$) 115.7, 78.1, 47.6, 45.5, 45.2, 38.6, 36.0, 21.4, 18.2, 16.9 (x2),14.4.

EXAMPLE 5

Enantiomerically Pure (3S,4S)-3,4-dimethylcyclopentanone (13)

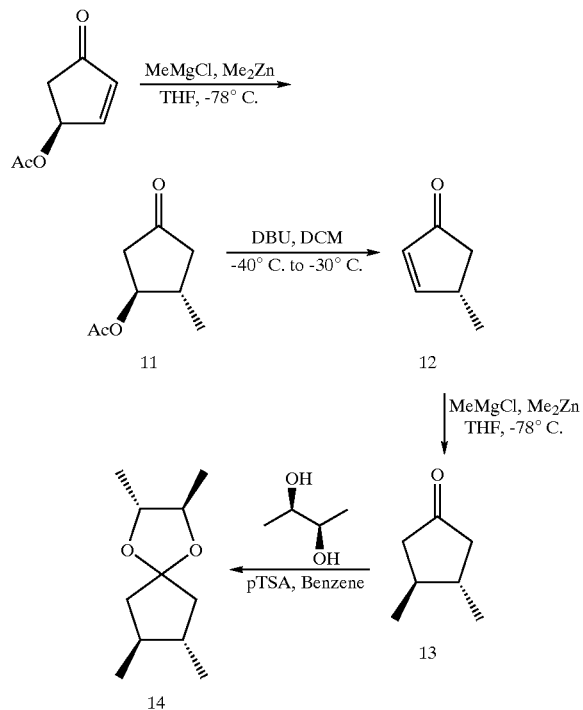

The Acetoxy Cyclopentanone 11

Methylmagnesium chloride (11.3 ml of a 3M solution in THF, 33.9 mmol) was added slowly to a stirred solution of dimethylzinc (17.0 ml of a 2M solution in toluene, 34.0 mmol) in THF (80 ml) at 0° C. under argon. After 20 minutes, the mixture was cooled to −78° C. and (S)-4-acetoxycyclopent-2-enone (4.33 g, 30.9 mmol) in THF (45 ml) was added dropwise over 1 hour. The reaction mixture was stirred for a further 20 minutes and then quenched by the addition of saturated ammonium chloride solution (20 ml). The reaction mixture was allowed to warm to room temperature, diluted with 1N hydrochloric acid (100 ml) and extracted with ether (3×200 ml). The organic layer was washed with brine (200 ml), dried (MgSO$_4$) and the solvent was removed under reduced pressure to yield the acetoxy cyclopentanone 11 as a solution in toluene which was used without further purification in the next step.

$v_{max}$(film)/cm$^{-1}$ 1737 (C=O).

$\delta_H$(400 MHz; CDCl$_3$) 5.01 (1H, m, CHOAc), 2.72 (1H, dd, J 19.0, 6.6), 2.59 (1H, m), 2.46 (1H, m), 2.24 (1H, dd, J 19.0, 4.6), 2.07 (3H, s, OCOMe), 1.95 (1H, dd, J 18.6, 5.7), 1.13 (3H, d, J 7.1, CHMe).

The Methylcyclopentanone 12

Acetoxy cyclopentanone 11 (approx. 30.9 mmol) in dichloromethane (40 ml) was added dropwise over 1 hour to a stirring solution of DBU (4.6 ml, 30.9 mmol) in dichloromethane (50 ml) at −40° C. under argon. The mixture was allowed to warm to −30° C. and stirred for 30 minutes before being quenched with dilute hydrochloric acid (20 ml). The reaction mixture was partitioned between ether (100 ml) and 1N HCl (150 ml). The organic layer was separated and the aqueous layer was further extracted with ether (2×100 ml). The combined ether layers were washed with brine, dried (MgSO$_4$) and the solvent was evaporated under reduced pressure. The residue was chromatographed (SiO$_2$, pentane-ether, 7:3) to give methylcyclopentenone 12 (1.51 g, 51% from (S)-4-acetoxycyclopent-2-enone).

$v_{max}$(film)/cm$^{-1}$ 1715 (C=O).

$\delta_H$(400 MHz; CDCl$_3$) 7.59 (1H, dd, J 5.6, 2.4, CH=CHC=O), 6.14 (1H, dd, J 5.6, 2.0, CH=CHC=O), 3.02 (1H, m), 2.60 (1H, dd, J 18.8, 6.3, CH$_A$H$_B$C=O), 1.95 (1H, dd, J 18.8, 2.2, CH$_A$H$_B$C=O) 1.21 (3H, d, J 7.1, CHMe).

The Dimethylcyclopentanone 13

Methylmagnesium chloride (5.2 ml of a 3M solution in ether, 15.6 mmol) was added slowly to a stirred solution of dimethylzinc (3.9 ml of a 2M solution in toluene, 7.8 mmol) in THF (20 ml) under argon at 0° C. After 30 minutes the mixture was cooled to −78° C. and 12 (0.67 g, 7.0 mmol) in THF (10 ml) was added dropwise over 1 hour. The reaction mixture was stirred for 20 minutes and then quenched by the addition of saturated ammonium chloride solution (10 ml). The reaction mixture was allowed to warm to room temperature, diluted with 1N hydrochloric acid (40 ml) and extracted with ether (3×50 ml). The organic layer was washed with brine (50 ml), dried (MgSO$_4$) and the solvent was removed under reduced pressure to yield 13 as a solution in toluene which was purified by column chromatography (SiO$_2$, pentane-ether, 95:5) to give the dimethylcyclopentanone 13 (0.45g, 52%).

$v_{max}$(film)/cm$^{-1}$ 1732 (C=O).

$\delta_H$(400 MHz; CDCl$_3$) 2.50–2.39 (2H, m), 1.89–1.72 (4H, m), 1.12 (6H, d, J 5.6, 2×Me).

Enantiomeric Purity of 13 was Established by Conversion to Acetal 14

14

The ketone 13 (0.25 g, 2.23 mmol), (2R,3R)-(−)-2,3-butanediol (0.23 ml, 2.45 mmol) and p-toluenesulphonic acid (0.042 g, 0.22 mmol) were refluxed together in benzene (10 ml) for 3 hours using a Dean-Stark trap. The reaction mixture was allowed to cool, taken up in ethyl acetate (100 ml), washed with saturated sodium bicarbonate solution, brine, dried (MgSO$_4$) and concentrated in vacuo to give 14 (0.21 g, 51%).

$\delta_C$(CDCl$_3$) 115.5, 78.0, 47.8, 40.1, 17.7, 16.9.

m/z (CI$^+$) 185 (M+H, 70%)

The acetal made from racemic (3RS,4RS)-3,4-dimethylketone has signals as shown below:

$\delta_C$(CDCl$_3$) 115.6, 115.5, 78.2, 78.1, 47.8, 47.5, 40.2, 40.0, 18.1, 17.7, 17.3, 16.9

EXAMPLE 6

Enantiomerically Pure (S)-3-methylcyclopentanone (16)

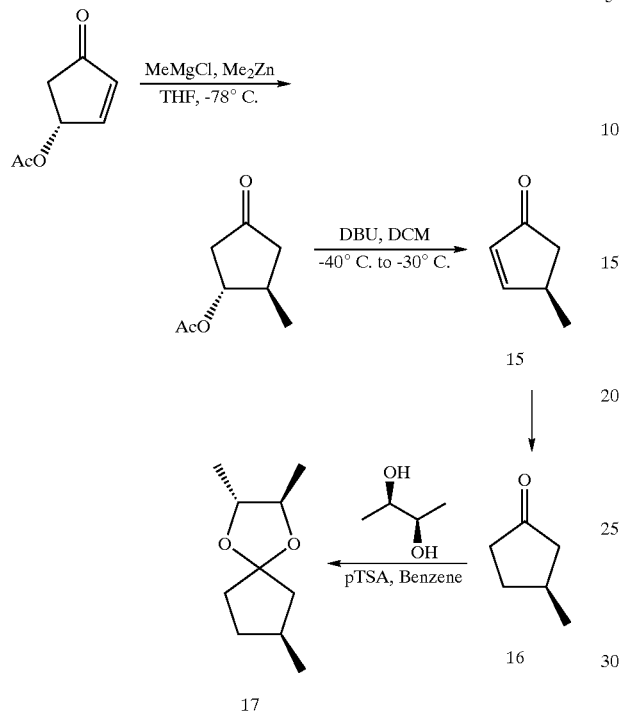

EXAMPLE 7

Enantiomerically Pure (3S,4S)-3-ethyl-4-methyl-cyclopentanone (20)

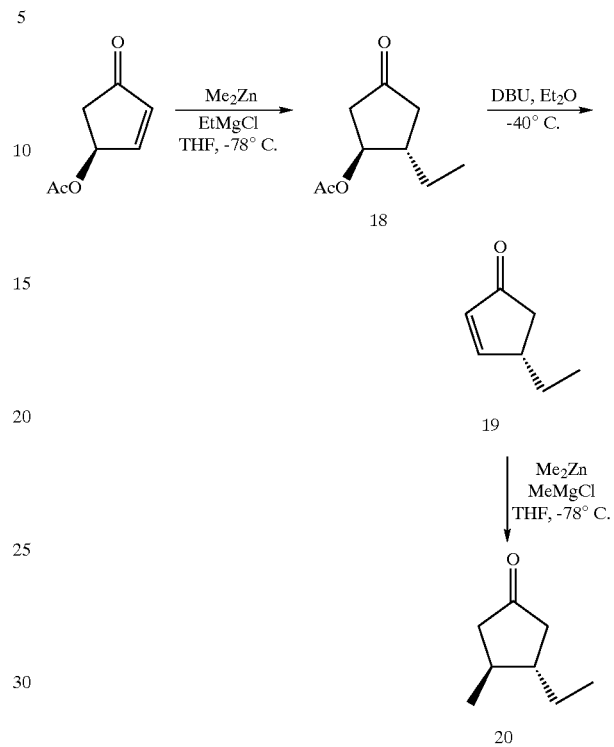

The Methylcyclopentenone 15

Compound 15 was prepared using the same method as 12.

The Methylcyclopentanone 16

A mixture of 15 (1.17 g, 12.2 mmol) and 10% palladium on charcoal (catalytic quantity) in ethyl acetate (30 ml) was shaken at 55 psi Hydrogen at 30° C. for 6 hours. The reaction mixture was filtered and the solvent was removed under reduced pressure. The residue was chromatographed (SiO$_2$, pentane-ether, 9:1) to give the 3-methylcyclopentanone 16 (1.09 g, 91%).

$v_{max}$(film)/cm$^{-1}$ (C=O) 1731.

$\delta_H$(400 MHz; CDCl$_3$) 2.42–2.08 (5H, m), 1.78 (1H, ddd, J 16.8, 9.3, 0.7), 1.51 (1H, m), 1.13 (3H, d, J 6.8).

The Acetal 17

The ketone 16 (0.25 g, 2.55 mmol), (2R,3R)-(−)-2,3-butanediol (0.26 ml, 2.80 mmol) and p-toluenesulphonic acid (0.05 g, 0.255 mmol) were refluxed together in benzene (10 ml) for 3 hours using a Dean-Stark trap. The reaction mixture was allowed to cool, taken up in ethyl acetate (100 ml), washed with saturated sodium bicarbonate solution, brine, dried (MgSO$_4$) and concentrated in vacuo to give the acetal 17 (0.20 g, 47%).

$\delta_H$(400 MHz; CDCl$_3$) 3.59 (2H, m), 2.08–1.17 (13H, m), 1.01 (3H, d, J 6.8, Me); $\delta_C$(CDCl$_3$) 117.4, 78.3, 78.0, 46.4, 38.0, 32.1, 20.6, 17.2, 17.1.

The acetal of the racemic 3-methylcyclopentanone has signals as shown below:

$\delta_C$(CDCl$_3$) 117.4, 78.3, 78.1 (x2), 78.0, 46.7, 46.4, 38.5, 38.0, 32.5, 32.1, 20.6, 20.2, 17.2, 17.1, 16.9 (x2).

The Acetoxy Cyclopentanone 18

Ethylmagnesium chloride (19.6 ml of a 2M solution in THF, 39.2 mmol) was added slowly to a stirred solution of dimethylzinc (19.6 ml of a 2M solution in toluene, 39.2 mmol) in THF (80 ml) at 0° C. under argon. After 20 minutes, the mixture was cooled to −78° C. and (S)-4-acetoxycyclopent-2-enone (5.0 g, 35.7 mmol) in THF (45 ml) was added dropwise over 1 hour. The reaction mixture was stirred for a further 20 minutes and then quenched by the addition of saturated ammonium chloride solution (20 ml). The reaction mixture was allowed to warm to room temperature, diluted with 1N hydrochloric acid (100 ml) and extracted with ether (3×200 ml). The organic layer was washed with brine (200 ml), dried (MgSO$_4$) and the solvent was removed under reduced pressure to yield the acetoxy cyclopentanone 18 as a solution in toluene which was used without further purification in the next step.

$v_{max}$(film)/cm$^{-1}$ 1741 (C=O).

$\delta_H$(400 MHz; CDCl$_3$) 5.10 (1H, m, CHOAc), 2.70 (1H, dd, J 19.3, 6.7), 2.57 (1H, ddd, J 18.5, 8.3, 1.2), 2.32–2.20 (2H, m), 2.07 (3H, s, OCOMe), 2.00 (1H, m), 1.62 (2H, m), 0.98 (3H, t, J 7.2, Me).

The Ethylcyclopentenone 19

Acetoxy cyclopentanone 18 (approx. 35.7 mmol) in dichloromethane (45 ml) was added dropwise over 1 hr to a stirring solution of DBU (5.34 ml, 35.7 mmol) in dichloromethane (100 ml) at −40° C. under argon. The mixture was allowed to warm to −30° C. and stirred for 30 minutes before being quenched with dilute hydrochloric acid (30 ml). The reaction mixture was partitioned between ether (100 ml) and 1N HCl (150 ml). The organic layer was separated and the aqueous layer was further extracted with ether (2×100 ml). The combined ether layers were washed with brine, dried (MgSO$_4$) and the solvent was evaporated under reduced pressure. The residue was chromatographed (SiO$_2$, pentane-ether, 8:2) to give ethylcyclopentenone 19 (3.4 g, 86% from (S)-4-acetoxycyclopent-2-enone).

$v_{max}$(film)/cm$^{-1}$ 1713 (C=O).

$\delta_H$(400 MHz; CDCl$_3$) 7.65 (1H, dd, J 5.6, 2.4, CH=CHC=O), 6.16 (11H, dd, J 5.6, 2.0, CH=CHC=O), 2.88 (1H, m), 2.54 (1H, dd, J 19.0, 6.3, CH$_A$H$_B$C=O), 2.02 (1H, dd, J 18.8, 2.2, CH$_A$H$_B$C=O) 1.63 (1H, m), 1.47 (1H, m), 0.99 (3H, t, J 7.6, Me).

The Cyclopentanone 20

Methylmagnesium chloride (22.5 ml of a 3M solution in ether, 67.5 mmol) was added slowly to a stirred solution of dimethylzinc (16.9 ml of a 2M solution in toluene, 33.8 mmol) in THF (100 ml) under argon at 0° C. After 30 minutes the mixture was cooled to −78° C. and 19 (3.37 g, 30.6 mmol) in THF (45 ml) was added dropwise over 1 hour. The reaction mixture was stirred for 20 minutes and then quenched by the addition of saturated ammonium chloride solution (25 ml). The reaction mixture was allowed to warm to room temperature, diluted with 1N hydrochloric acid (100 ml) and extracted with ether (3×100 ml). The organic layer was washed with brine (50 ml), dried (MgSO$_4$) and the solvent was removed under reduced pressure to yield 20 as a solution in toluene which was purified by column chromatography (SiO$_2$, pentane-ether, 95:5) to give the cyclopentanone 20 (2.4 g, 62%).

$v_{max}$(film)/cm$^{-1}$ 1738 (C=O).

$\delta_H$(400 MHz; CDCl$_3$) 2.50–2.40 (2H, m), 1.92–1.60 (6H, m), 1.12 (3H, d, J 6.1, Me), 0.93 (3H, t, J 6.5, Me).

Conversion to an Acetal

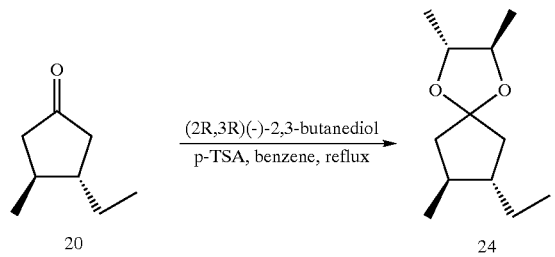

The ketone 20 (0.22 g, 1.74 mmol), (2R,3R)-(−)-2,3-butanediol (0.18 ml, 1.91 mmol) and p-toluenesulphonic acid (0.033 g, 0.174 mmol) were refluxed together in benzene (10 ml) for 3 hours using a Dean-Stark trap. The reaction mixture was allowed to cool, taken up in ethyl acetate (100 ml), washed with saturated sodium bicarbonate solution, brine, dried (MgSO$_4$) and concentrated in vacuo to give 24 (0.19 g, 55%).

$\delta_C$(CDCl$_3$) 115.6, 78.1 (x2), 47.6, 47.1, 44.9, 38.2, 26.2, 19.3, 18.2, 16.9, 14.2; m/z (CI$^+$) 199 (M+H, 82%).

EXAMPLE 8

Enantiomerically Pure (R)-3-ethylcyclopentanone (21)

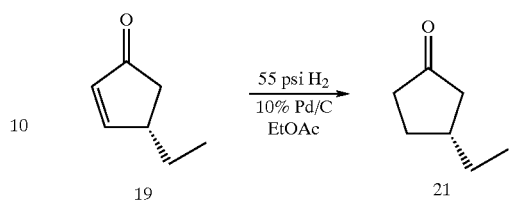

A mixture of 19 (3.4 g, 30.9 mmol) and 10% palladium on charcoal (catalytic quantity) in ethyl acetate (50 ml) was shaken at 55 psi in hydrogen at 30° C. for 6 hours. The reaction mixture was filtered and the solvent was removed under reduced pressure. The residue was chromatographed (SiO$_2$, pentane-ether, 9:1) to give the 3-ethylcyclopentanone 21 (3.4 g, 98%).

$v_{max}$(film)/cm$^{-1}$ 1737 (C=O).

$\delta_H$(400 MHz; CDCl$_3$) 2.38 (1H, dd, J 18.1, 7.3), 2.29 (1H, dd, J 16.1, 8.8), 2.21–2.04 (4H, m), 1.79 (1H, ddd, J 18.1, 9.8, 1.1), 1.47 (2H, m), 0.95 (3H, t, J 7.6, Me).

Conversion to Acetal 25

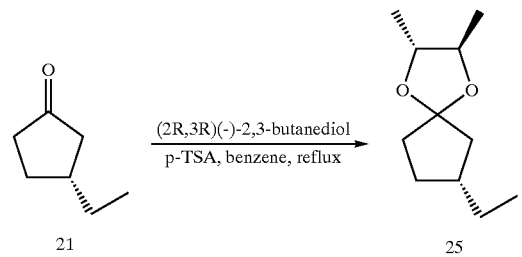

The ketone 21 (0.098 g, 0.874 mmol), (2R,3R)-(−)-2,3-butanediol (0.088 ml, 0.96 mmol) and p-toluenesulphonic acid (0.017 g, 0.087 mmol) were refluxed together in benzene (10 ml) for 3 hours using a Dean-Stark trap. The reaction mixture was allowed to cool, taken up in ethyl acetate (100 ml), washed with saturated sodium bicarbonate solution, brine, dried (MgSO$_4$) and concentrated in vacuo to give 25 (0.12 g, 73%).

$\delta_C$(CDCl$_3$) 117.2, 78.2, 78.1, 44.5, 39.8, 38.0, 30.1, 28.6, 17.0, 16.9, 12.5; m/z (CI$^+$) 185 (M+H, 75%)

EXAMPLES 10 & 11

(3R,4R)-3 ethyl-4-methyl-cyclopentanone (22) and (S)-3-ethyl-cyclopentanone (23)

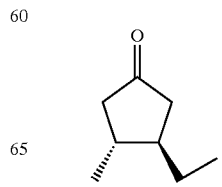

-continued

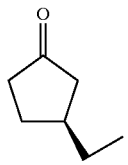
23

Compounds 22 and 23 were made using the procedure of the previous examples.

Conversion to acetals 26, 27

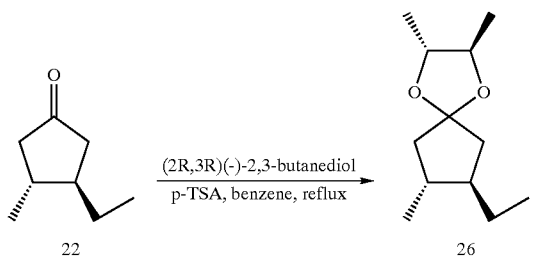

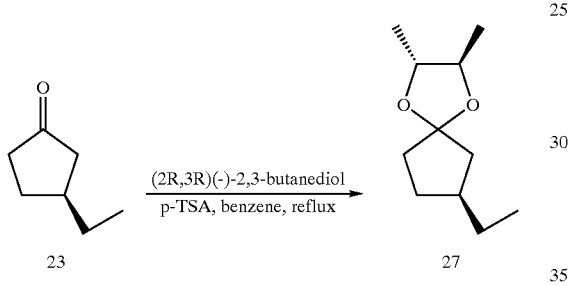

The enantiomeric purity of ketone 22 was confirmed by making acetal 26 using the previously described procedure.

$\delta_C$(CDCl$_3$) 115.7, 78.2, 78.1, 47.3, 46.9, 44.6, 38.0, 26.6, 19.3, 18.8, 17.3, 17.2, 14.2; m/z (CI$^+$) 199 (M+H, 80%)

The enantiomeric purity of ketone 23 was also confirmed by making acetal 26 using the previously described procedure.

$\delta_C$(CDCl$_3$) 117.2, 78.3, 78.1, 44.2, 39.3, 37.6, 29.7, 28.8, 17.2, 12.5; m/z (CI$^+$) 185 (M+H, 78%).

What is claimed is:

1. A method of making an enantiomerically pure compound of the formula (I) or (II):

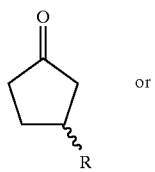

(I)

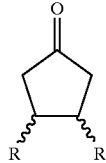

(II)

wherein R and R' represent $C_1$–$C_{10}$ alkyl, $C_2$–$C_{10}$ alkenyl or $C_3$–$C_{10}$ cycloalkyl and the wedges signify (S)- or (R)-stereochemistry, the substituents in compound (II) being trans, which method comprises:

conjugate addition of an organometallic nucleophile that provides a group R as defined above to a compound of the formula (III) or (IV):

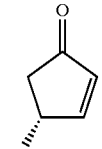

(III)

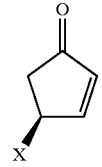

(IV)

wherein the conjugate addition is carried out by adding the chiral cyclopentenone of formula (III) or (IV) to an organo-Grignard reagent or to an organo-lithium reagent in the presence of a dialkylzinc or zinc chloride or a copper (I) salt or a trialkylaluminium in a solvent at a temperature from −100° C. to 0° C., and wherein X represents a leaving group to give a trans 3,4-disubstituted addition product of formula (V) or (VI) in which R and X are as previously defined;

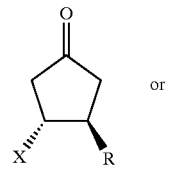

(V)

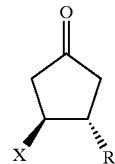

(VI)

eliminating the leaving-group X from the addition product of formula (V) or (VI) to give an (R)- or (S)-4-alkyl or 4-alkenyl cyclopent-2-en-1-one of formula (VII) or (VIII)

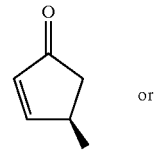

(VII)

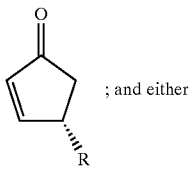

(i) hydrogenation of the compound of formula (VII) or (VIII) to give a cyclopentanone of formula (I) or (ii) conjugate addition of a second organometallic nucleophile that provides a group R' as defined above to the compound of formula (VII) or (VIII) to give a trans 3,4-disubstituted addition product of formula (II).

2. The method of claim 1, when used to make an (S)-compound of formula (I).

3. The method of claim 1, when used to make an (R)-compound of formula (I).

4. The method of claim 1, when used to make a (3S,4S)-compound of formula (II).

5. The method of claim 1, when used to make a (3R,4R)-compound of formula (II).

6. The method of claim 1, when used to make a compound in which R and R' (if present) represent methyl, ethyl or n-propyl.

7. The method of claim 1, when used to make any of the following compounds:
 (S)-3-methylcyclopentanone;
 (R)-3-methylcyclopentanone;
 (S)-3-ethylcyclopentanone;
 (R)-3-ethylcyclopentanone;
 (S)-3-n-propylcyclopentanone;
 (R)-3-n-propylcyclopentanone;
 (3S,4S)-3,4-dimethyl-cyclopentanone;
 (3R,4R)-3,4-dimethyl-cyclopentanone;
 (3S,4S)-3,4-diethyl-cyclopentanone;
 (3R,4R)-3,4-diethyl-cyclopentanone;
 (3S,4S)-3-ethyl-4-methyl-cyclopentanone;
 (3R,4R)-3-ethyl-4-methyl-cyclopentanone;
 (3S,4S)-3-methyl-4-propyl-cyclopentanone;
 (3R,4R)-3-methyl-4-propyl-cyclopentanone;
 (3S,4S)-3-ethyl-4-propyl-cyclopentanone;
 (3R,4R)-3-ethyl-4-propyl-cyclopentanone.

8. The method of claim 1, wherein the solvent is selected from tetrahydrofuran, 1,4-dioxane, n-heptane, toluene, diethyl ether and t-butyl methyl ether.

9. A method of making an enantiomerically pure compound of the formula (I) or (II):

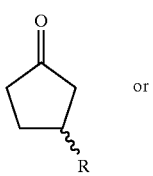

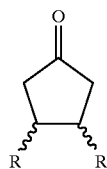

wherein R and R' represent $C_1$–$C_{10}$ alkyl, $C_2$–$C_{10}$ alkenyl or $C_3$–$C_{10}$ cycloalkyl and the wedges signify (S)- or (R)-stereochemistry, the substituents in compound (II) being trans, which method comprises;

conjugate addition of an organometallic nucleophile that provides a group R as defined above to a compound of the formula (III) or (IV);

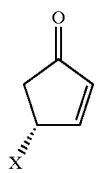

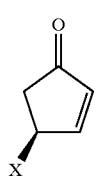

wherein X represent a leaving group to give a trans 3,4-disubstituted addition product of formula (V) or (VI) in which R and X are as previously defined;

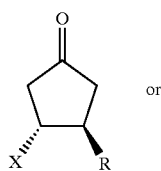

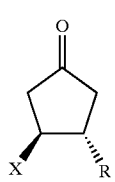

eliminating the leaving-group X from the addition product of formula (V) or (VI) by treating the trans 3,4-disubstituted addition product of formula (V) or (VI) with a strong organic base or with a metal hydride in a solvent to live an (R)- or (S)-4-alkyl or 4-alkenyl cyclopent-2-en-1-one of formula (VII) or (VIII)

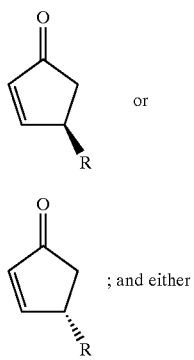

(i) hydrogenation of the compound of formula (VII) or (VIII) to give a cyclopentanone of formula (I) or (ii) conjugate addition of a second organometallic nucleophile that provides a group R' as defined above to the compound of formula (VII) or (VIII) to give a trans 3,4-disubstituted addition product of formula (II).

10. The method of claim 9, wherein the base or hydride is selected from 1,8-diazabicyclo[5.4.0]undec-7-ene (DBU), 1,5-diazabicyclo[4.3.0]non-5-ene (DBN), 1,1,3,3-tetramethyl guanidine (TMG), lithium hydride and sodium hydride.

11. The method of claim 9, wherein the solvent is selected from dichloromethane, diethyl ether, tetrahydrofuran, t-butyl methyl ether and 14-dioxane.

12. The method of claim 1, wherein the elimination product of formula (VII) or (VIII) is treated with hydrogen at a pressure of 1–30 atmospheres at a temperature in the range 0–60° C. in a solvent and in the presence of a hydrogenation catalyst to give a compound of formula (I).

13. The method of claim 12, wherein the hydrogenation catalyst is selected from palladium on charcoal, platinum oxide, Raney nickel, and rhodium on alumina.

14. The method of claim 12, wherein in the solvent is ethyl acetate or methanol.

15. A method of making an enantiomerically pure compound of the formula (I) or (II):

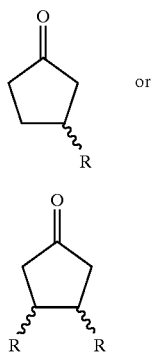

wherein R and R' represent $C_1$–$C_{10}$ alkyl, $C_2$–$C_{10}$ alkenyl or $C_3$–$C_{10}$ cycloalkyl and the wedges signify (S)- or (R)-stereochemistry, the substituents in compound (II) being trans, which method comprises:

conjugate addition of an organometallic nucleophile that provides a group R as defined above to a compound of the formula (III) or (IV):

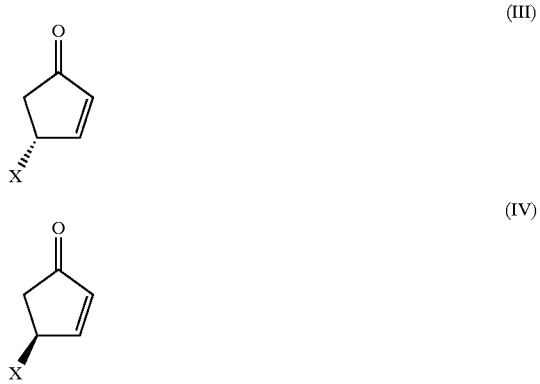

wherein X represents a leaving group to give a trans 3,4-disubstituted addition product of formula (V) or (VI) in which R and X are as previously defined;

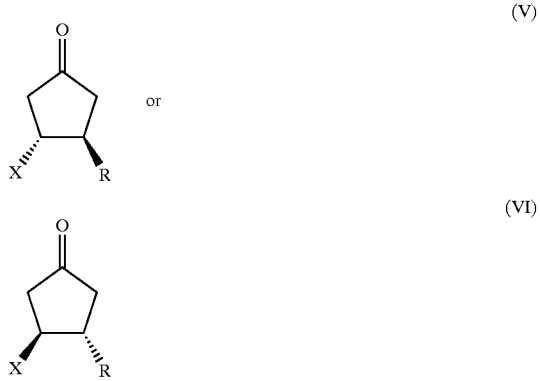

eliminating the leaving-group X from the addition product of formula (V) or (VI) to give an (R)- or (S)-4-alkyl or 4-alkenyl cyclopent-2-en-1-one of formula (VII) or (VIII)

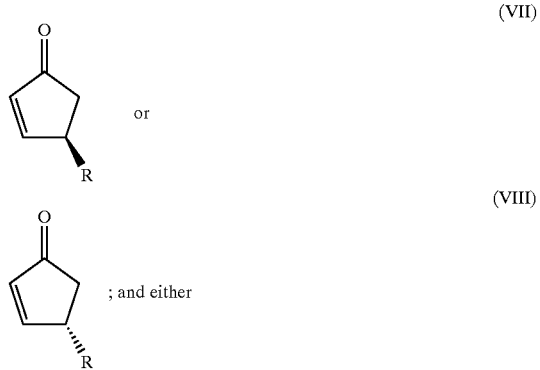

(i) hydrogenation of the compound of formula (VII) or (VIII) to give a cyclopentanone of formula (I) or (ii) (ii) conjugate addition of a second organometallic nucleophile that provides a group R' as defined above to the compound of formula (VII) or (VIII) to give a trans 3,4-disubstituted addition product of formula (II), wherein the conjugate addition is curried out by treating the elimination product of formula (VII) or (VIII) with a second organo-Grignard reagent or with a second organo-lithium reagent in the presence of a dialkylzinc or zinc chloride or a copper (I) salt or a trialkylaluminium in a solvent at a temperature from −100° C. to 0° C. to produce a compound of formula (II).

16. The method of claim 15, wherein the solvent is selected from tetrahydrofuran, 1,4-dioxane, n-heptane, toluene, diethyl ether and t-butyl methyl ether.

17. The method of claim 1, wherein the leaving group X in the compound of formula (III) or (IV) is acetoxy.

18. The method of claim 1, wherein the leaving group X in the compound of formula (III) or (IV) is halogen or sulfonic acid ester group.

19. The method of claim 1, wherein the elimination product of formula (VII) or (VIII) is produced by treating the trans 3,4-disubstituted addition product of formula (V) or (VI) with a strong organic base or with a metal hydride in a solvent.

* * * * *